US012751862B2

(12) United States Patent
Argento et al.

(10) Patent No.: US 12,751,862 B2
(45) Date of Patent: Oct. 6, 2026

(54) ADJUSTABLE FLOW GLAUCOMA SHUNTS AND ASSOCIATED SYSTEMS AND METHODS

(71) Applicant: Shifamed Holdings, LLC, Campbell, CA (US)

(72) Inventors: Claudio Argento, Felton, CA (US); Katherine Sapozhnikov, Campbell, CA (US); Richard Lilly, San Jose, CA (US); Christopher J. Engelman, Los Gatos, CA (US); Jean Orth, Morgan Hill, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 749 days.

(21) Appl. No.: 17/765,199

(22) PCT Filed: Oct. 9, 2020

(86) PCT No.: PCT/US2020/055144
§ 371 (c)(1),
(2) Date: Mar. 30, 2022

(87) PCT Pub. No.: WO2021/072317
PCT Pub. Date: Apr. 15, 2021

(65) Prior Publication Data

US 2022/0387217 A1 Dec. 8, 2022

Related U.S. Application Data

(60) Provisional application No. 62/937,680, filed on Nov. 19, 2019, provisional application No. 62/937,676,
(Continued)

(51) Int. Cl.
*A61F 9/007* (2006.01)
*A61M 27/00* (2006.01)

(52) U.S. Cl.
CPC ....... *A61F 9/00781* (2013.01); *A61M 27/002* (2013.01); *A61F 2250/0004* (2013.01)

(58) Field of Classification Search
CPC ........ A61F 9/00781; A61F 2250/0004; A61M 27/002
See application file for complete search history.

(56) References Cited

U.S. PATENT DOCUMENTS 4,401,107 A 8/1983 Harber et al.
4,402,681 A 9/1983 Haas et al.
(Continued)

FOREIGN PATENT DOCUMENTS

AU 2014200171 1/2014
AU 2014201621 B2 3/2016
(Continued)

OTHER PUBLICATIONS

"Collins Dictionary, Textured definition and meaning, 2024, Collins Dictionary, https://www.collinsdictionary.com/dictionary/english/textured" (Year: 2024).*
(Continued)

*Primary Examiner* — Kai H Weng
*Assistant Examiner* — Katherine-Ph Minh Pham
(74) *Attorney, Agent, or Firm* — Ashurst Perkins Coie US

(57) ABSTRACT

The present technology is directed to adjustable flow glaucoma shunts, systems, and methods for making and using such devices. In many of the embodiments described herein, the shunts include a drainage element configured to fluidly couple an anterior chamber of an eye and a target outflow location, such as a subconjunctival bleb space. The shunts can further include a flow control assembly coupled to the drainage element and configured to control the flow of fluid (e.g., aqueous) therethrough. The shunts can further include an outer membrane or bladder that encases the flow control
(Continued)

assembly. The outer membrane can include a plurality of apertures that fluidly couple an interior of the outer membrane with an environment exterior to the outer membrane.

23 Claims, 14 Drawing Sheets

Related U.S. Application Data filed on Nov. 19, 2019, provisional application No. 62/913,694, filed on Oct. 10, 2019, provisional application No. 62/913,700, filed on Oct. 10, 2019.

(56) References Cited

U.S. PATENT DOCUMENTS

| | | | |
|---|---|---|---|
| 4,595,390 | A | 6/1986 | Hakim et al. |
| 5,070,697 | A | 12/1991 | Van Zeggeren |
| 5,123,906 | A | 6/1992 | Kelman |
| 5,476,445 | A | 12/1995 | Baerveldt et al. |
| 5,601,094 | A | 2/1997 | Reiss |
| 5,792,118 | A | 8/1998 | Kurth et al. |
| 6,007,511 | A | 12/1999 | Prywes |
| 6,077,298 | A | 6/2000 | Tu et al. |
| 6,077,299 | A | 6/2000 | Adelberg et al. |
| 6,203,513 | B1 | 3/2001 | Yaron et al. |
| 6,261,256 | B1 | 7/2001 | Ahmed |
| 6,450,984 | B1 | 9/2002 | Lynch et al. |
| 6,508,779 | B1 | 1/2003 | Suson |
| 6,589,203 | B1 | 7/2003 | Mitrev |
| 6,626,858 | B2 | 9/2003 | Lynch et al. |
| 6,638,239 | B1 | 10/2003 | Bergheim et al. |
| 6,666,841 | B2 | 12/2003 | Gharib et al. |
| 6,736,791 | B1 | 5/2004 | Tu et al. |
| 6,789,447 | B1 | 9/2004 | Zinck |
| 7,025,740 | B2 | 4/2006 | Ahmed |
| 7,207,965 | B2 | 4/2007 | Simon |
| 7,354,416 | B2 | 4/2008 | Quiroz-Mereado et al. |
| 7,458,953 | B2 | 12/2008 | Peyman |
| 7,699,882 | B2 | 4/2010 | Stamper et al. |
| 7,717,872 | B2 | 5/2010 | Shetty |
| 7,947,008 | B2 | 5/2011 | Grahn et al. |
| 8,012,134 | B2 | 9/2011 | Claude et al. |
| 8,157,759 | B2 | 4/2012 | Castillejos |
| 8,206,333 | B2 | 6/2012 | Schmidt et al. |
| 8,206,440 | B2 | 6/2012 | Guarnieri |
| 8,298,240 | B2 | 10/2012 | Giger et al. |
| 8,308,701 | B2 | 11/2012 | Horvath et al. |
| 8,414,635 | B2 | 4/2013 | Hyodoh et al. |
| 8,506,515 | B2 | 8/2013 | Burns et al. |
| 8,540,659 | B2 | 9/2013 | Berlin |
| 8,579,848 | B2 | 11/2013 | Field et al. |
| 8,585,629 | B2 | 11/2013 | Grabner et al. |
| 8,663,303 | B2 | 3/2014 | Horvath et al. |
| 8,702,639 | B2 | 4/2014 | Van Der Mooren et al. |
| 8,721,702 | B2 | 5/2014 | Romoda et al. |
| 8,753,305 | B2 | 6/2014 | Field et al. |
| 8,758,290 | B2 | 6/2014 | Horvath et al. |
| 8,765,210 | B2 | 7/2014 | Romoda et al. |
| 8,771,220 | B2 | 7/2014 | Nissan et al. |
| 8,801,766 | B2 | 8/2014 | Reitsamer et al. |
| 8,828,070 | B2 | 9/2014 | Romoda et al. |
| 8,852,136 | B2 | 10/2014 | Horvath et al. |
| 8,852,137 | B2 | 10/2014 | Horvath et al. |
| 8,852,256 | B2 | 10/2014 | Horvath et al. |
| 8,882,781 | B2 | 11/2014 | Smedley et al. |
| 8,915,877 | B2 | 12/2014 | Cunningham et al. |
| 8,932,247 | B2 | 1/2015 | Stergiopulos |
| 8,974,511 | B2 | 3/2015 | Horvath et al. |
| 9,017,276 | B2 | 4/2015 | Horvath et al. |
| 9,095,411 | B2 | 8/2015 | Horvath et al. |
| 9,095,413 | B2 | 8/2015 | Romoda et al. |
| 9,113,994 | B2 | 8/2015 | Horvath et al. |
| 9,125,723 | B2 | 9/2015 | Horvath et al. |
| 9,192,516 | B2 | 11/2015 | Horvath et al. |
| 9,226,851 | B2 | 1/2016 | Gunn |
| 9,271,869 | B2 | 3/2016 | Horvath et al. |
| 9,283,115 | B2 | 3/2016 | Lind et al. |
| 9,283,116 | B2 | 3/2016 | Romoda et al. |
| 9,289,324 | B2 | 3/2016 | Johnson et al. |
| 9,326,891 | B2 | 5/2016 | Horvath et al. |
| 9,375,347 | B2 | 6/2016 | Stergiopulos |
| 9,393,153 | B2 | 7/2016 | Horvath et al. |
| 9,555,410 | B2 | 1/2017 | Brammer et al. |
| 9,585,789 | B2 | 3/2017 | Silvestrini et al. |
| 9,585,790 | B2 | 3/2017 | Horvath et al. |
| 9,592,154 | B2 | 3/2017 | Romoda et al. |
| 9,610,195 | B2 | 4/2017 | Horvath |
| 9,636,254 | B2 | 5/2017 | Yu et al. |
| 9,636,255 | B2 | 5/2017 | Haffner et al. |
| 9,655,778 | B2 | 5/2017 | Tyler |
| 9,655,779 | B2 | 5/2017 | Bigler et al. |
| 9,693,900 | B2 | 7/2017 | Gallardo Inzunza |
| 9,693,901 | B2 | 7/2017 | Horvath et al. |
| 9,757,276 | B2 | 9/2017 | Penhasi |
| 9,808,373 | B2 | 11/2017 | Horvath et al. |
| 9,877,866 | B2 | 1/2018 | Horvath et al. |
| 9,883,969 | B2 | 2/2018 | Horvath et al. |
| 9,980,854 | B2 | 5/2018 | Horvath et al. |
| 10,004,638 | B2 | 6/2018 | Romoda et al. |
| 10,080,682 | B2 | 9/2018 | Horvath et al. |
| 10,085,884 | B2 | 10/2018 | Reitsamer et al. |
| 10,154,924 | B2 | 12/2018 | Clauson et al. |
| 10,159,600 | B2 | 12/2018 | Horvath et al. |
| 10,195,078 | B2 | 2/2019 | Horvath et al. |
| 10,195,079 | B2 | 2/2019 | Horvath et al. |
| 10,231,871 | B2 | 3/2019 | Hill |
| 10,238,536 | B2 | 3/2019 | Olson et al. |
| 10,285,853 | B2 | 5/2019 | Rangel-Friedman et al. |
| 10,307,293 | B2 | 6/2019 | Horvath et al. |
| 10,314,743 | B2 | 6/2019 | Romoda et al. |
| 10,322,267 | B2 | 6/2019 | Hakim |
| 10,335,030 | B2 | 7/2019 | Alhourani |
| 10,342,703 | B2 | 7/2019 | Siewert et al. |
| 10,363,168 | B2 | 7/2019 | Schieber et al. |
| 10,369,048 | B2 | 8/2019 | Horvath et al. |
| 10,405,903 | B1 | 9/2019 | Biesinger et al. |
| 10,463,537 | B2 | 11/2019 | Horvath et al. |
| 10,470,927 | B2 | 11/2019 | Horvath et al. |
| 10,492,948 | B2 | 12/2019 | Baerveldt |
| 10,524,958 | B2 | 1/2020 | Camras et al. |
| 10,524,959 | B2 | 1/2020 | Horvath |
| 10,596,035 | B2 | 3/2020 | Stergiopulos et al. |
| 10,716,663 | B2 | 7/2020 | Salahieh et al. |
| 10,758,412 | B2 | 9/2020 | Velasquez |
| 10,912,675 | B2 | 2/2021 | Lubatschowski |
| 10,952,897 | B1 | 3/2021 | Smith |
| 10,960,074 | B2 | 3/2021 | Berdahl |
| 11,007,061 | B2 | 5/2021 | Passman et al. |
| 11,039,954 | B2 | 6/2021 | Cohen et al. |
| 11,058,581 | B2 | 7/2021 | Mixter et al. |
| 11,065,154 | B1 | 7/2021 | Sponsel et al. |
| 11,083,624 | B2 | 8/2021 | Stein et al. |
| 11,122,975 | B2 | 9/2021 | Rodger et al. |
| 11,166,847 | B2 | 11/2021 | Badawi et al. |
| 11,166,848 | B2 | 11/2021 | Mixter et al. |
| 11,166,849 | B2 | 11/2021 | Mixter et al. |
| 11,291,585 | B2 | 4/2022 | Schultz et al. |
| 11,517,477 | B2 | 12/2022 | Lilly et al. |
| 11,529,258 | B2 | 12/2022 | Chang et al. |
| 11,737,920 | B2 | 8/2023 | Chang et al. |
| 11,766,355 | B2 | 9/2023 | Argento et al. |
| 11,865,283 | B2 | 1/2024 | Schultz et al. |
| 12,220,350 | B2 | 2/2025 | Mixter et al. |
| 12,226,343 | B2 | 2/2025 | Mixter et al. |
| 2001/0011585 | A1 | 8/2001 | Cassidy et al. |
| 2002/0177891 | A1 | 11/2002 | Miles et al. |
| 2002/0193725 | A1 | 12/2002 | Odrich |
| 2003/0079329 | A1 | 5/2003 | Yaron et al. |
| 2003/0127090 | A1 | 7/2003 | Gifford et al. |
| 2003/0163079 | A1 | 8/2003 | Burnett |
| 2003/0183008 | A1 | 10/2003 | Bang et al. |
| 2004/0010219 | A1 | 1/2004 | McCusker et al. |
| 2004/0162545 | A1 | 8/2004 | Brown et al. |

(56) References Cited

U.S. PATENT DOCUMENTS

2004/0190153 A1 9/2004 Esch
2004/0193095 A1 9/2004 Shadduck
2004/0254520 A1 12/2004 Porteous et al.
2005/0049578 A1 3/2005 Tu et al.
2005/0059956 A1 3/2005 Varner et al.
2005/0182350 A1 8/2005 Nigam
2005/0196424 A1 9/2005 Chappa
2006/0004317 A1 1/2006 Mauge et al.
2006/0069340 A1 3/2006 Simon
2006/0155300 A1 7/2006 Stamper et al.
2006/0212113 A1 9/2006 Shaolian et al.
2006/0276739 A1 12/2006 Brown
2007/0010837 A1 1/2007 Tanaka
2007/0078371 A1 4/2007 Brown et al.
2007/0088432 A1 4/2007 Solovay et al.
2007/0239161 A1 10/2007 Giger et al.
2007/0265646 A1 11/2007 McCoy et al.
2007/0299487 A1 12/2007 Shadduck
2008/0077071 A1 3/2008 Yaron et al.
2008/0103440 A1 5/2008 Ferren et al.
2008/0119891 A1 5/2008 Miles et al.
2008/0125691 A1* 5/2008 Yaron ................ A61F 9/00781 604/9
2008/0228127 A1 9/2008 Burns et al.
2008/0277332 A1 11/2008 Liu
2009/0012483 A1 1/2009 Blott et al.
2009/0036818 A1 2/2009 Grahn et al.
2009/0043321 A1 2/2009 Conston et al.
2009/0243956 A1 10/2009 Keilman et al.
2009/0259236 A2 10/2009 Burnett et al.
2009/0287136 A1 11/2009 Castillejos
2009/0314970 A1 12/2009 McAvoy et al.
2009/0326432 A1 12/2009 Schmidt et al.
2009/0326517 A1 12/2009 Bork et al.
2010/0114006 A1 5/2010 Baerveldt
2010/0234791 A1 9/2010 Lynch et al.
2010/0241077 A1 9/2010 Geipel et al.
2010/0249691 A1 9/2010 Van Der Mooren et al.
2010/0331757 A1 12/2010 Claude et al.
2011/0105986 A1 5/2011 Bronstein et al.
2012/0022429 A1 1/2012 Silvestrini et al.
2012/0065570 A1 3/2012 Yeung et al.
2012/0071814 A1* 3/2012 Fallin ...................... A61M 1/84 604/537
2012/0078220 A1* 3/2012 Fallin ................ A61M 25/0043 604/500
2012/0089073 A1 4/2012 Cunningham, Jr.
2012/0232461 A1 9/2012 Seaver et al.
2013/0085440 A1 4/2013 Bohm et al.
2013/0131577 A1 5/2013 Bronstein et al.
2013/0144202 A1 6/2013 Field et al.
2013/0150773 A1 6/2013 Nissan et al.
2013/0150776 A1 6/2013 Bohm et al.
2013/0158381 A1 6/2013 Rickard
2013/0160445 A1* 6/2013 Olson ..................... F03G 7/062 60/527
2013/0197621 A1 8/2013 Ryan et al.
2013/0199646 A1 8/2013 Brammer et al.
2013/0205923 A1 8/2013 Brammer et al.
2013/0211312 A1 8/2013 Gelvin
2013/0267887 A1* 10/2013 Kahook .............. A61F 9/00781 604/9
2013/0317412 A1 11/2013 Dacquay et al.
2013/0338564 A1 12/2013 Rickard et al.
2014/0046439 A1 2/2014 Dos Santos et al.
2014/0081195 A1 3/2014 Clauson et al.
2014/0213958 A1 7/2014 Clauson et al.
2014/0236066 A1 8/2014 Horvath et al.
2014/0236067 A1 8/2014 Horvath et al.
2014/0236068 A1* 8/2014 Van Der Mooren ........................ A61F 9/00781 604/9
2014/0276332 A1* 9/2014 Crimaldi ............. A61F 9/00781 604/8
2014/0309611 A1 10/2014 Wilt et al.
2014/0336560 A1 11/2014 Hakim
2015/0011926 A1 1/2015 Reitsamer et al.
2015/0034217 A1 2/2015 Vad
2015/0045716 A1 2/2015 Gallardo Inzunza
2015/0057592 A1 2/2015 Gunn
2015/0142049 A1 5/2015 Delgado et al.
2015/0230843 A1 8/2015 Palmer et al.
2015/0257931 A1 9/2015 Sanchez et al.
2015/0265469 A1 9/2015 Olson et al.
2015/0313603 A1 11/2015 Bodewadt et al.
2016/0058615 A1* 3/2016 Camras ............... A61F 9/00781 604/9
2016/0058616 A1 3/2016 Camras et al.
2016/0067093 A1 3/2016 Johnson et al.
2016/0151179 A1 6/2016 Favier et al.
2016/0220794 A1 8/2016 Negre
2016/0256317 A1 9/2016 Horvath et al.
2016/0256318 A1 9/2016 Horvath et al.
2016/0256319 A1 9/2016 Horvath et al.
2016/0256320 A1 9/2016 Horvath et al.
2016/0287439 A1 10/2016 Stergiopulos
2016/0296371 A1 10/2016 Gelvin
2016/0354244 A1 12/2016 Horvath et al.
2016/0354245 A1 12/2016 Horvath et al.
2017/0027582 A1 2/2017 Khoury et al.
2017/0071791 A1 3/2017 Piven
2017/0087016 A1 3/2017 Camras
2017/0172797 A1 6/2017 Horvath et al.
2017/0172798 A1 6/2017 Horvath et al.
2017/0172799 A1 6/2017 Horvath
2017/0246034 A1 8/2017 Hill
2017/0312125 A1 11/2017 Clauson et al.
2017/0348149 A1 12/2017 Stergiopulos et al.
2017/0348150 A1 12/2017 Horvath et al.
2018/0014828 A1 1/2018 Fonte et al.
2018/0028361 A1 2/2018 Haffner et al.
2018/0028366 A1 2/2018 Tout et al.
2018/0092775 A1 4/2018 de Juan, Jr. et al.
2018/0147089 A1 5/2018 Horvath et al.
2018/0177633 A1 6/2018 Haffner et al.
2018/0206878 A1 7/2018 Uspenski et al.
2018/0250166 A1 9/2018 Lubatschowski
2018/0333296 A1 11/2018 Heitzmann et al.
2019/0000673 A1 1/2019 Fjield et al.
2019/0021907 A1 1/2019 Horvath et al.
2019/0038462 A1 2/2019 Vandiest et al.
2019/0038463 A1 2/2019 Kasic
2019/0046356 A1 2/2019 Laroche
2019/0060118 A1 2/2019 Hill
2019/0121278 A1 4/2019 Kawamura et al.
2019/0133826 A1 5/2019 Horvath et al.
2019/0142632 A1 5/2019 Badawi et al.
2019/0151079 A1 5/2019 Zaldivar
2019/0167475 A1 6/2019 Horvath et al.
2019/0240069 A1 8/2019 Horvath et al.
2019/0247231 A1 8/2019 McClunan
2019/0254873 A1 8/2019 Camras et al.
2019/0274881 A1 9/2019 Romoda et al.
2019/0274882 A1 9/2019 Romoda et al.
2019/0307608 A1 10/2019 Lee et al.
2019/0344057 A1 11/2019 Cima et al.
2019/0350758 A1 11/2019 Horvath et al.
2019/0353269 A1 11/2019 Ossmer et al.
2019/0358086 A1 11/2019 Camras et al.
2019/0374384 A1 12/2019 Xie et al.
2020/0069469 A1 3/2020 Horvath et al.
2020/0085620 A1 3/2020 Euteneuer et al.
2020/0121503 A1 4/2020 Badawi et al.
2020/0121504 A1 4/2020 Stegmann et al.
2020/0129332 A1 4/2020 Van Der Mooren et al.
2020/0170839 A1 6/2020 Borrmann et al.
2020/0179171 A1 6/2020 Crimaldi et al.
2020/0197157 A1 6/2020 Shmukler et al.
2020/0197178 A1* 6/2020 Vecchio ............. A61B 5/02055
2020/0214891 A1 7/2020 Bigler et al.
2020/0229977 A1 7/2020 Mixter et al.
2020/0229980 A1 7/2020 Horvath
2020/0229981 A1 7/2020 Mixter et al.

(56) References Cited

U.S. PATENT DOCUMENTS

| | | | |
|---|---|---|---|
| 2020/0229982 | A1 | 7/2020 | Mixter et al. |
| 2020/0246188 | A1 | 8/2020 | Horvath et al. |
| 2020/0253725 | A1 | 8/2020 | Hadba et al. |
| 2020/0261271 | A1 | 8/2020 | Horvath et al. |
| 2020/0276050 | A1 | 9/2020 | Simons et al. |
| 2020/0306086 | A1 | 10/2020 | Da Silva Curiel et al. |
| 2020/0345549 | A1 | 11/2020 | Lu et al. |
| 2020/0376239 | A1 | 12/2020 | Heilman et al. |
| 2021/0015665 | A1 | 1/2021 | Hacker et al. |
| 2021/0030590 | A1 | 2/2021 | Blanda et al. |
| 2021/0038158 | A1 | 2/2021 | Haffner et al. |
| 2021/0069486 | A1 | 3/2021 | Hakim |
| 2021/0106462 | A1 | 4/2021 | Sherwood et al. |
| 2021/0128357 | A1 | 5/2021 | de Juan, Jr. et al. |
| 2021/0137736 | A1 | 5/2021 | Cavuto et al. |
| 2021/0137737 | A1 | 5/2021 | Burns et al. |
| 2021/0161713 | A1 | 6/2021 | Bouremel et al. |
| 2021/0196516 | A1 | 7/2021 | Ianchulev |
| 2021/0205132 | A1 | 7/2021 | Horvath et al. |
| 2021/0212858 | A1 | 7/2021 | Tran et al. |
| 2021/0251806 | A1 | 8/2021 | Schultz et al. |
| 2021/0282922 | A1 | 9/2021 | Cohen-Tzemaeh et al. |
| 2021/0298948 | A1 | 9/2021 | Haffner et al. |
| 2021/0315806 | A1 | 10/2021 | Haffner |
| 2021/0330499 | A1 | 10/2021 | Wardle et al. |
| 2022/0087865 | A1 | 3/2022 | Argento et al. |
| 2022/0142818 | A1 | 5/2022 | Chang et al. |
| 2022/0160545 | A1 | 5/2022 | Mixter et al. |
| 2022/0160546 | A1 | 5/2022 | Mixter et al. |
| 2022/0168146 | A1 | 6/2022 | Badawi et al. |
| 2022/0202613 | A1 | 6/2022 | Chang et al. |
| 2022/0203078 | A1 | 6/2022 | May |
| 2022/0241565 | A1 | 8/2022 | Nae et al. |
| 2022/0249155 | A1 | 8/2022 | Lilly et al. |
| 2022/0249285 | A1 | 8/2022 | Chang et al. |
| 2022/0265974 | A1 | 8/2022 | Saul et al. |
| 2022/0273491 | A1 | 9/2022 | Brown |
| 2022/0339035 | A1 | 10/2022 | Lilly et al. |
| 2022/0354695 | A1 | 11/2022 | Badawi et al. |
| 2022/0387216 | A1 | 12/2022 | Schultz et al. |
| 2023/0086856 | A1 | 3/2023 | Chang et al. |
| 2023/0092196 | A1 | 3/2023 | Argento et al. |
| 2023/0146222 | A1 | 5/2023 | Kancerevycius et al. |
| 2023/0201544 | A1 | 6/2023 | Schultz et al. |
| 2023/0201545 | A1 | 6/2023 | Alexander et al. |
| 2023/0233378 | A1 | 7/2023 | Chang et al. |
| 2023/0240891 | A1 | 8/2023 | Lilly et al. |
| 2023/0285192 | A1 | 9/2023 | Chang et al. |
| 2024/0139029 | A1 | 5/2024 | Chang et al. |
| 2024/0173169 | A1 | 5/2024 | Schultz et al. |
| 2024/0277522 | A1 | 8/2024 | Schultz et al. |
| 2024/0277523 | A1 | 8/2024 | Schultz et al. |
| 2024/0325697 | A1 | 10/2024 | Schultz et al. |
| 2024/0399122 | A1 | 12/2024 | Bronez et al. |
| 2025/0010044 | A1 | 1/2025 | Schultz et al. |
| 2025/0082501 | A1 | 3/2025 | Bronez et al. |

FOREIGN PATENT DOCUMENTS

| | | | |
|---|---|---|---|
| AU | 2016201445 | B2 | 3/2016 |
| AU | 2018200325 | A1 | 2/2018 |
| AU | 2017274654 | | 12/2018 |
| AU | 2020201818 | | 4/2020 |
| AU | 2017439185 | | 5/2020 |
| AU | 2018412569 | | 10/2020 |
| BR | 112017025859 | A2 | 8/2018 |
| BR | 112020008969 | | 10/2020 |
| CA | 2987953 | A1 | 12/2016 |
| CA | 3067172 | | 12/2018 |
| CA | 3080713 | | 5/2019 |
| CA | 3093160 | | 9/2019 |
| CN | 101360523 | A | 2/2009 |
| CN | 101965211 | A | 2/2011 |
| CN | 103476371 | | 12/2013 |
| CN | 104490515 | | 4/2015 |
| CN | 106726124 | | 5/2017 |
| CN | 108743016 | A | 11/2018 |
| CN | 111405875 | | 7/2020 |
| CN | 112431950 | | 3/2021 |
| CO | 2020011460 | | 11/2020 |
| DE | 10217061 | | 3/2003 |
| DE | 102010015447 | | 10/2011 |
| DE | 102010015447 | A1 | 10/2011 |
| DE | 102017124885 | | 4/2019 |
| DE | 102017124885 | A1 | 4/2019 |
| DE | 102018112065 | A1 | 11/2019 |
| DE | 102019204846 | | 10/2020 |
| DE | 102019204846 | A1 | 10/2020 |
| EP | 1292256 | A1 | 3/2003 |
| EP | 1380317 | | 1/2004 |
| EP | 1737531 | A2 | 1/2007 |
| EP | 2552369 | | 1/2017 |
| EP | 3302381 | A1 | 4/2018 |
| EP | 1765234 | | 10/2019 |
| EP | 2999430 | | 11/2019 |
| EP | 2677981 | | 4/2020 |
| EP | 3659495 | | 6/2020 |
| EP | 3518846 | | 8/2020 |
| EP | 3666236 | | 8/2020 |
| EP | 3687374 | | 8/2020 |
| EP | 3706653 | | 9/2020 |
| EP | 3730104 | | 10/2020 |
| EP | 3735947 | | 11/2020 |
| EP | 3773377 | | 2/2021 |
| EP | 3846747 | | 7/2021 |
| EP | 3846748 | | 7/2021 |
| EP | 3329884 | | 8/2021 |
| EP | 2389138 | | 9/2021 |
| EP | 3870120 | | 9/2021 |
| EP | 3313335 | | 11/2021 |
| ES | 2725550 | | 9/2019 |
| GB | 2602434 | | 9/2022 |
| HK | 1252748 | | 5/2019 |
| HU | E043303 | | 8/2019 |
| JP | 2001-523519 | | 11/2001 |
| JP | 2013505065 | | 2/2013 |
| JP | 5576427 | B2 | 8/2014 |
| JP | 2017526504 | | 9/2017 |
| JP | 2018-501010 | | 1/2018 |
| JP | 2018519892 | | 7/2018 |
| JP | 2018130580 | | 8/2018 |
| JP | 2018529466 | | 10/2018 |
| JP | 2019517366 | | 6/2019 |
| JP | 2019205934 | | 12/2019 |
| JP | 2020049361 | | 4/2020 |
| KR | 2018015684 | A | 2/2018 |
| KR | 20190019966 | | 2/2019 |
| KR | 20200021551 | | 2/2020 |
| KR | 20200059305 | | 5/2020 |
| PL | 2640455 | | 8/2019 |
| PT | 2640455 | | 5/2019 |
| RU | 2687764 | | 5/2019 |
| RU | 2018142990 | | 6/2020 |
| SG | 11202008604 | | 10/2020 |
| TR | 201906873 | | 6/2019 |
| WO | WO1996019249 | | 6/1996 |
| WO | WO2004073564 | | 9/2004 |
| WO | WO2004081613 | | 9/2004 |
| WO | WO2007011302 | A1 | 1/2007 |
| WO | WO2007087061 | | 8/2007 |
| WO | WO2009111645 | | 9/2009 |
| WO | WO2010111528 | | 9/2010 |
| WO | WO2011034740 | | 3/2011 |
| WO | WO2012040380 | | 3/2012 |
| WO | WO2012113450 | | 8/2012 |
| WO | WO2014130574 | | 8/2014 |
| WO | WO2016/033270 | | 3/2016 |
| WO | WO2016100500 | | 6/2016 |
| WO | WO2016149425 | | 9/2016 |
| WO | WO2016196841 | A1 | 12/2016 |
| WO | WO2017058656 | | 4/2017 |
| WO | WO2018229766 | | 12/2018 |
| WO | WO2019094004 | A1 | 5/2019 |
| WO | WO2019165053 | | 8/2019 |

(56) References Cited

FOREIGN PATENT DOCUMENTS

| | | |
|---|---|---|
| WO | WO2019172940 | 9/2019 |
| WO | WO2020049508 | 3/2020 |
| WO | WO2020150663 | 7/2020 |
| WO | WO2020215068 | 10/2020 |
| WO | WO2020223491 | 11/2020 |
| WO | WO2020231993 | 11/2020 |
| WO | WO2020247365 | 12/2020 |
| WO | WO2020261184 | 12/2020 |
| WO | WO2021007294 | 1/2021 |
| WO | WO2021007296 | 1/2021 |
| WO | WO2021028703 | 2/2021 |
| WO | WO2021068078 | 4/2021 |
| WO | WO2021072315 | 4/2021 |
| WO | WO2021072317 | 4/2021 |
| WO | WO2021113730 | 6/2021 |
| WO | WO2021142255 | 7/2021 |
| WO | WO2021151007 | 7/2021 |
| WO | WO2021163566 | 8/2021 |
| WO | WO2021168130 | 8/2021 |
| WO | WO2021174298 | 9/2021 |
| WO | WO2021176332 | 9/2021 |
| WO | WO2021188952 | 9/2021 |
| WO | WO2021204312 | 10/2021 |
| WO | WO2021212007 | 10/2021 |
| WO | WO2021230887 | 11/2021 |
| WO | WO2022159723 | 7/2022 |
| WO | WO2022175681 | 8/2022 |
| WO | WO2022220861 | 10/2022 |
| WO | WO2023004067 | 1/2023 |
| WO | WO2023278452 | 1/2023 |
| WO | WO2023009366 | 2/2023 |
| WO | WO2023063961 | 4/2023 |
| WO | WO2023064491 | 4/2023 |
| WO | WO2023091307 | 5/2023 |
| WO | WO2023107486 | 6/2023 |
| WO | WO2023215461 | 11/2023 |
| WO | WO2024026397 | 2/2024 |
| WO | WO2024030949 | 2/2024 |
| WO | WO2024097723 | 5/2024 |
| WO | WO2024097743 | 5/2024 |
| WO | WO2024108125 | 5/2024 |
| WO | WO2024220861 | 10/2024 |
| WO | WO2025054477 | 3/2025 |
| WO | WO2025054502 | 3/2025 |
| ZA | 201708295 | 5/2020 |

OTHER PUBLICATIONS

International Search Report and Written Opinion received for PCT Application No. PCT/US24/25489, Applicant: Shifamed Holdings, LLC, Date of Mailing: Sep. 9, 2024, 18 pages.

International Search Report and Written Opinion received for PCT Application No. PCT/US23/80290, filed on Nov. 17, 2023, Applicant: Shifamed Holdings, LLC, Date of Mailing: May 15, 2024, 12 pages.

English translation of Japanese Office Action received for Application No. 2022-521301, Applicant: Shifamed Holdings, LLC, Date of Mailing: Jun. 3, 2024, 3 pages.

Extended European Search Report received for EP Application No. 23158246.1, Applicant: Shifamed Holdings, LLC, Date of Mailing: Aug. 7, 2023, 7 pages.

International Search Report and Written Opinion received for PCT Application No. PCT/US23/20973, filed on May 4, 2023, Applicant: Shifamed Holdings, LLC, Date of Mailing: Sep. 21, 2023, 15 pages.

Extended European Search Report received for EP Application No. 20874212.2, Applicant: Shifamed Holdings, LLC, Date of Mailing: Oct. 18, 2023, 8 pages.

Extended European Search Report received for EP Application No. 20875070.3, Applicant: Shifamed Holdings, LLC, Date of Mailing: Dec. 19, 2023, 7 pages.

International Search Report and Written Opinion received for PCT Application No. PCT/US23/71501, filed on Aug. 2, 2023, Applicant: Shifamed Holdings, LLC, Date of Mailing: Jan. 18, 2024, 20 pages.

Extended European Search Report received for EP Application No. 21787751.3; Applicant: Shifamed Holdings, LLC, Date of Mailing: Mar. 15, 2024, 8 pages.

International Search Report and Written Opinion received for PCT Application No. PCT/US23/71116, filed on Jul. 27, 2023, Applicant: Shifamed Holdings, LLC, Date of Mailing: Mar. 1, 2024, 12 pages.

International Search Report and Written Opinion received for PCT Application No. PCT/US22/35324, filed on Jun. 28, 2022, Applicant: Shifamed Holdings, LLC, Date of Mailing: Nov. 22, 2022, 12 pages.

International Search Report and Written Opinion received for PCT Application No. PCT/US22/37917, filed on Jul. 21, 2022, Applicant: Shifamed Holdings, LLC, Date of Mailing: Dec. 15, 2022, 15 pages.

Keulegan et al. "Pressure Losses for Fluid Flow in Curved Pipes," Journal of Research of the National Bureau of Standards, vol. 18, Jan. 31, 1937 (Jan. 31, 1937), 26 pages.

Olsen et al. "Human sclera: thickness and surface area," American Journal of Ophthalmology, vol. 125, Issue. 2, https://pubmed.ncbi.nlm.nih.gov/9467451, Feb. 1, 1998 (Feb. 1, 1998), 1 page.

International Search Report and Written Opinion received for PCT Application No. PCT/US22/048863, filed on Nov. 3, 2022, Applicant: Shifamed Holdings, LLC, Date of Mailing: Feb. 16, 2023, 13 pages.

International Search Report and Written Opinion received for PCT Application No. PCT/US22/52002, filed on Dec. 6, 2022, Applicant: Shifamed Holdings, LLC, Date of Mailing: Mar. 21, 2023, 11 pages.

International Search Report and Written Opinion received for PCT Application No. PCT/US22/46604, filed on Oct. 13, 2022, Applicant: Shifamed Holdings, LLC, Date of Mailing: Mar. 30, 2023, 11 pages.

International Search Report and Written Opinion received for PCT Application No. PCT/US18/43158, filed on Jul. 20, 2018, Applicant: Shifamed Holdings, LLC, Date of Mailing: Nov. 23, 2018, 12 pages.

International Search Report and Written Opinion received for PCT Application No. PCT/US20/41159, filed on Jul. 8, 2020, Applicant: Shifamed Holdings, LLC, Date of Mailing: Oct. 28, 2020, 13 pages.

International Search Report and Written Opinion received for PCT Application No. PCT/US20/41152, filed on Jul. 8, 2020, Applicant: Shifamed Holdings, LLC, Date of Mailing: Oct. 28, 2020, 13 pages.

International Search Report and Written Opinion received for PCT Application No. PCT/US20/14186, filed on Jan. 17, 2020, Applicant: Shifamed Holdings, LLC, Date of Mailing: Jun. 4, 2020, 13 pages.

International Search Report and Written Opinion received for PCT Application No. PCT/US21/14774, filed on Jan. 22, 2021, Applicant: Shifamed Holdings, LLC, Date of Mailing: May 12, 2021, 10 pages.

International Search Report and Written Opinion received for PCT Application No. PCT/US21/17962, filed on Feb. 12, 2021, Applicant: Shifamed Holdings, LLC, Date of Mailing: Jun. 7, 2021, 12 pages.

International Search Report and Written Opinion received for PCT Application No. PCT/US21/23238, filed on Mar. 19, 2021, Applicant: Shifamed Holdings, LLC, Date of Mailing: Jul. 8, 2021, 10 pages.

International Search Report and Written Opinion received for PCT Application No. PCT/US21/18601, filed on Feb. 18, 2021, Applicant: Shifamed Holdings, LLC, Date of Mailing: Jul. 19, 2021, 12 pages.

International Search Report and Written Opinion received for PCT Application No. PCT/US21/27742, filed on Apr. 16, 2021, Applicant: Shifamed Holdings, LLC, Date of Mailing: Oct. 7, 2021, 13 pages.

International Search Report and Written Opinion received for PCT Application No. PCT/US21/47013, filed on Aug. 20, 2021, Applicant: Shifamed Holdings, LLC, Date of Mailing: Nov. 26, 2021, 28 pages.

(56) References Cited

OTHER PUBLICATIONS

International Search Report and Written Opinion received for PCT Application No. PCT/US21/49140, filed on Sep. 3, 2021, Applicant: Shifamed Holdings, LLC, Date of Mailing: Dec. 7, 2021, 22 pages.
International Search Report and Written Opinion received for PCT Application No. PCT/US21/55258, filed on Oct. 15, 2021, Applicant: Shifamed Holdings, LLC, Date of Mailing: Feb. 28, 2022, 18 pages.
International Search Report and Written Opinion received for PCT Application No. PCT/US22/13336, filed on Jan. 21, 2022, Applicant: Shifamed Holdings, LLC, Date of Mailing: Apr. 11, 2022, 9 pages.
International Search Report and Written Opinion received for PCT Application No. PCT/US20/55144, filed on Oct. 9, 2020, Applicant: Shifamed Holdings, LLC, Date of Mailing: Feb. 1, 2021, 16 pages.
International Search Report and Written Opinion received for PCT Application No. PCT/US20/55141, filed on Oct. 9, 2020, Applicant: Shifamed Holdings, LLC, Date of Mailing: Jan. 29, 2021, 11 pages.
Extended European Search Report received for EP Application No. 21744394.4, Applicant: Shifamed Holdings, LLC, Date of Mailing: Jan. 26, 2024, 7 pages.
Extended European Search Report received for EP Application No. 22743262.2; Applicant: Shifamed Holdings, LLC, Date of Mailing: Oct. 28, 2024, 8 pages.
Collins Dictionary, Textured definition and meaning, 2024, Collins Dictionary, https://www.collinsdictionary.com/dictionary/english/textured, Year: 2024, 1 page.
English translation of Chinese Office Action received for CN Application No. 201880060989.1; Applicant: Shifamed Holdings, LLC, Date of Mailing: Oct. 18, 2024, 9 pages.
English translation of Japanese Office Action received for Application No. 2022-521302; Applicant: Shifamed Holdings, LLC, Date of Mailing: Dec. 24, 2024, 7 pages.
Extended European Search Report received for EP Application No. 21937177.0, Applicant: Shifamed Holdings, LLC, Date of Mailing: Jan. 16, 2025, 6 pages.
International Search Report and Written Opinion received for PCT Application No. PCT/US2024/045656, Applicant: Shifamed Holdings, LLC, Date of Mailing: Feb. 5, 2025, 15 pages.
International Search Report and Written Opinion received for PCT Application No. PCT/US2024/059574, Applicant: Shifamed Holdings, LLC, Date of Mailing: Feb. 19, 2025, 12 pages.
International Search Report and Written Opinion received for PCT Application No. PCT/US2024/053649, Applicant: Shifamed Holdings, LLC, Date of Mailing: Feb. 14, 2025, 13 pages.

* cited by examiner

ADJUSTABLE FLOW GLAUCOMA SHUNTS AND ASSOCIATED SYSTEMS AND METHODS

CROSS-REFERENCE TO RELATED APPLICATION(S)

This application is a 35 U.S.C. § 371 U.S. National Phase application of International Patent Application No. PCT/US2020/055144, filed Oct. 9, 2020, and titled ADJUSTABLE FLOW GLAUCOMA SHUNTS AND ASSOCIATED SYSTEMS AND METHODS, which claims priority to the following provisional patent applications:

U.S. Provisional Patent Application No. 62/913,694, filed Oct. 10, 2019;

U.S. Provisional Patent Application No. 62/913,700, filed Oct. 10, 2019;

U.S. Provisional Patent Application No. 62/937,676, filed Nov. 19, 2019; and

U.S. Provisional Patent Application No. 62/937,680, filed Nov. 19, 2019.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present technology relates to adjustable flow glaucoma shunts and methods for making and using such devices.

BACKGROUND

Glaucoma is a degenerative ocular condition involving damage to the optic nerve that can cause progressive and irreversible vision loss. Glaucoma is frequently associated with ocular hypertension, an increase in pressure within the eye, and may result from an increase in production of aqueous humor ("aqueous") within the eye and/or a decrease in the rate of outflow of aqueous from within the eye into the blood stream. Aqueous is produced in the ciliary body at the boundary of the posterior and anterior chambers of the eye. It flows into the anterior chamber and eventually into the venous vessels of the eye. Glaucoma is typically caused by a failure in mechanisms that transport aqueous out of the eye and into the blood stream.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

Figure 1A:
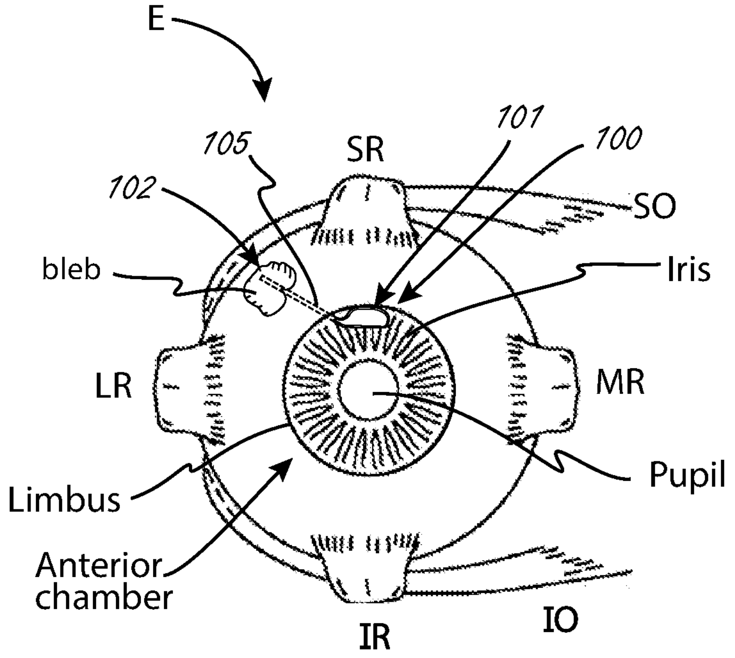
FIG. 1A is simplified front view of an eye E with an implanted shunt configured in accordance with an embodiment of the present technology.

The present technology is directed to adjustable flow glaucoma shunts, systems, and methods for making and using such devices. In many of the embodiments described herein, the shunts include a drainage element (e.g., a flow tube) having a first opening, a second opening, and a lumen extending between the first opening and the second opening. The first opening can be positioned in the anterior chamber, and the second opening can be positioned in a target outflow location, such as a subconjunctival bleb space. The shunts can further include a flow control assembly coupled to the drainage element and configured to control the flow of fluid (e.g., aqueous) through at least one of the first opening or the second opening. For example, in some embodiments the flow control assembly is coupled to the drainage element proximate the second opening and controls the flow of fluid as it exits the drainage tube. In other embodiments, the flow control assembly is coupled to the drainage element proximate the first opening and controls the flow of fluid as it enters the drainage tube. Regardless of its orientation, the shunts can further include an outer membrane or bladder that encases the flow control assembly. The outer membrane can include a plurality of apertures that fluidly couple an interior of the outer membrane with an environment exterior to the outer membrane.

Specific details of various embodiments of the present technology are described below with reference to FIGS. 1A-10D. Although many of the embodiments are described below with respect to adjustable flow glaucoma shunts and associated methods, other embodiments are within the scope of the present technology. Additionally, other embodiments of the present technology can have different configurations, components, and/or procedures than those described herein. For instance, shunts configured in accordance with the present technology may include additional elements and features beyond those described herein, or other embodiments may not include several of the elements and features shown and described herein. Moreover, the use of the term "shunt" herein generally refers to the overall devices described herein, but in some aspects the term "shunt" and "tube" are used interchangeably.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

Although certain embodiments herein are described in terms of shunting fluid from an anterior chamber of an eye, one of skill in the art will appreciate that the present technology can be readily adapted to shunt fluid from and/or between other portions of the eye, or, more generally, from and/or between a first body region and a second body region. Moreover, while the certain embodiments herein are described in the context of glaucoma treatment, any of the embodiments herein, including those referred to as "glaucoma shunts" or "glaucoma devices" may nevertheless be used and/or modified to treat other diseases or conditions, including other diseases or conditions of the eye or other body regions. For example, the systems described herein can be used to treat diseases characterized by increased pressure and/or fluid build-up, including but not limited to heart failure (e.g., heart failure with preserved ejection fraction, heart failure with reduced ejection fraction, etc.), pulmonary failure, renal failure, hydrocephalus, and the like. Moreover, while generally described in terms of shunting aqueous, the systems described herein may be applied equally to shunting other fluid, such as blood or cerebrospinal fluid, between the first body region and the second body region.

The headings provided herein are for convenience only and do not interpret the scope or meaning of the claimed present technology.

A. Implantable Shunts for Glaucoma Treatment

Glaucoma refers to a group of eye diseases associated with damage to the optic nerve which eventually result in vision loss and blindness. As noted above, glaucoma is a degenerative ocular condition characterized by an increase in pressure within the eye resulting from an increase in production of aqueous within the eye and/or a decrease in the rate of outflow of aqueous from within the eye into the blood stream. The increased pressure leads to injury of the optic nerve over time. Unfortunately, patients often do not present with symptoms of increased intraocular pressure until the onset of glaucoma. As such, patients typically must be closely monitored once increased pressure is identified even if they are not symptomatic. The monitoring continues over the course of the disease so clinicians can intervene early to stem progression of the disease. Monitoring pressure requires patients to visit a clinic site on a regular basis which is expensive, time-consuming, and inconvenient. The early stages of glaucoma are typically treated with drugs (e.g., eye drops) and/or laser therapy. When drug/laser treatments no longer suffice, however, surgical approaches can be used. Surgical or minimally invasive approaches primarily attempt to increase the outflow of aqueous from the anterior chamber to the blood stream either by the creation of alternative fluid paths or the augmentation of the natural paths for aqueous outflow.

Figure 1B:
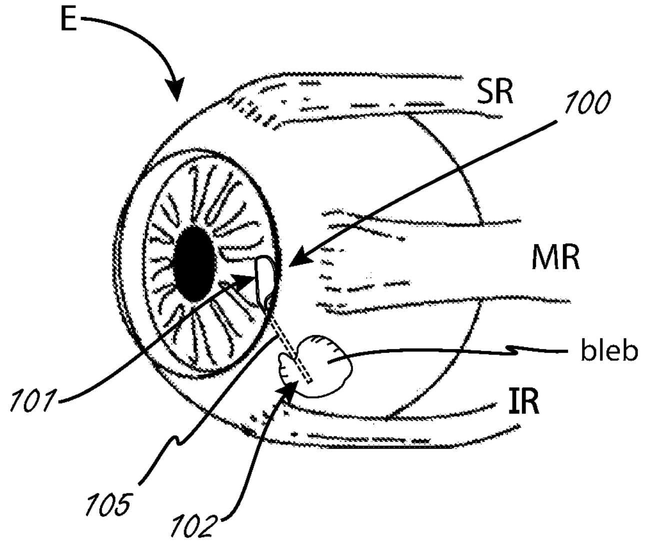
FIG. 1B is an isometric view of the eye and implanted shunt of FIG. 1A.

FIGS. 1A and 1B illustrate a human eye E and suitable location(s) in which a shunt may be implanted within the eye E in accordance with embodiments of the present technology. More specifically, FIG. 1A is a simplified front view of the eye E with an implanted shunt 100, and FIG. 1B is an isometric view of the eye E and shunt 100 of FIG. 1A. Referring first to FIG. 1A, the eye E includes a number of muscles to control its movement, including a superior rectus SR, inferior rectus IR, lateral rectus LR, medial rectus MR, superior oblique SO, and inferior oblique IO. The eye E also includes an iris, pupil, and limbus.

Referring to FIGS. 1A and 1B together, shunt 100 can have a drainage element 105 (e.g., a drainage tube) positioned such that an inflow portion 101 is positioned in an anterior chamber of the eye E, and an outflow portion 102 is positioned at a different location within the eye E, such as a bleb space. The shunt 100 can be implanted in a variety of orientations. For example, when implanted, the drainage element 105 may extend in a superior, inferior, medial, and/or lateral direction from the anterior chamber. Depending upon the design and orientation of the shunt 100, the outflow portion 102 can be placed in a number of different suitable outflow locations (e.g., between the choroid and the sclera, between the conjunctiva and the sclera, etc.).

Outflow resistance can change over time for a variety of reasons, e.g., as the outflow location goes through its healing process after surgical implantation of a shunt (e.g., shunt 100) or further blockage in the drainage network from the anterior chamber through the trabecular meshwork, Schlemm's canal, the collector channels, and eventually into the vein and the body's circulatory system. Accordingly, a clinician may desire to modify the shunt after implantation to either increase or decrease the outflow resistance in response to such changes or for other clinical reasons. For example, in many procedures the shunt is modified at implantation to temporarily increase its outflow resistance. After a period of time deemed sufficient to allow for healing of the tissues and stabilization of the outflow resistance, the modification to the shunt is reversed, thereby decreasing the outflow resistance. In another example, the clinician may implant the shunt and after subsequent monitoring of intraocular pressure determine a modification of the drainage rate through the shunt is desired. Such modifications can be invasive, time-consuming, and/or expensive for patients. If such a procedure is not followed, however, there is a high likelihood of creating hypotony (excessively low eye pressure), which can result in further complications, including damage to the optic nerve. In contrast, intraocular shunting systems configured in accordance with embodiments of the present technology allow the clinician to selectively adjust the flow of fluid through the shunt after implantation without additional invasive surgical procedures.

The shunts described herein can be implanted having a first drainage rate and subsequently remotely adjusted to achieve a second drainage rate. The adjustment can be based on the needs of the individual patient. For example, the shunt may be implanted at a first lower flow rate and subsequently adjusted to a second higher flow rate as clinically necessary. The shunts described herein can be delivered using either ab interno or ab externo implant techniques, and can be delivered via needles. The needles can have a variety of shapes and configurations to accommodate the various shapes of the shunts described herein. For example, in some embodiments, the needles may be hinged to facilitate implantation through the sclera. Details of the implant procedure, the implant devices, and bleb formation are described in greater detail in International Patent Application No. PCT/US20/41152, filed Jul. 8, 2020, the disclosure of which is hereby incorporated by reference herein for all purposes.

In many of the embodiments described herein, the flow control assemblies are configured to introduce features that selectively impede or attenuate fluid flow through the shunt during operation. In this way, the flow control assemblies can incrementally or continuously change the flow resistance through the shunt to selectively regulate pressure and/or flow. The flow control assemblies configured in accordance with the present technology can accordingly adjust the level of interference or compression between a number of different positions, and accommodate a multitude of variables (e.g., IOP, aqueous production rate, native aqueous outflow resistance, and/or native aqueous outflow rate) to precisely regulate flow rate through the shunt.

The disclosed actuators and fluid resistors can all be operated using externally delivered (e.g., non-invasive) energy. This feature allows such devices to be implanted in the patient and then modified/adjusted over time without further invasive surgeries or procedures for the patient. Further, because the devices disclosed herein may be actuated via energy, such devices do not require any additional power to maintain a desired orientation or position. Rather, the actuators/fluid resistors disclosed herein can maintain a desired position/orientation without power. This can significantly increase the usable lifetime of such devices and enable such devices to be effective long after the initial implantation procedure.

B. Selected Embodiments of Adjustable Flow Glaucoma Shunts

Figure 2A:
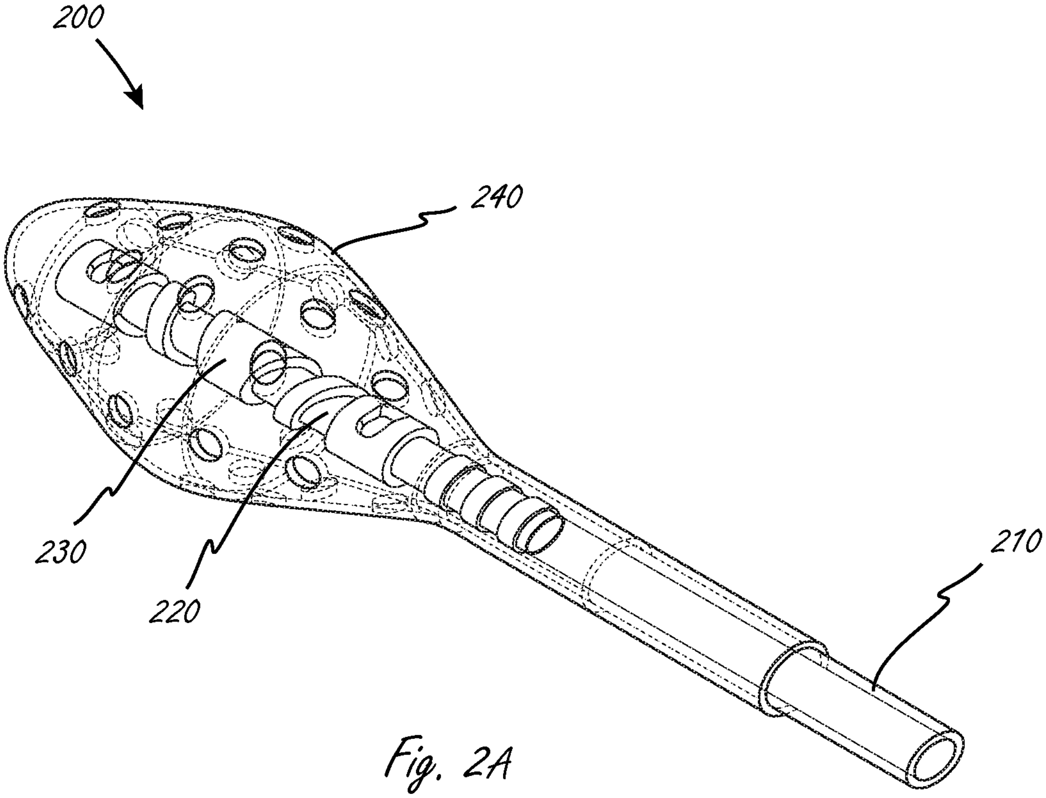
FIGS. 2A-2G illustrate an adjustable flow glaucoma shunt configured in accordance with an embodiment of the present technology.

FIGS. 2A-9 illustrate embodiments of adjustable flow glaucoma shunt devices, along with particular components and features associated with such devices. FIG. 2A, for example, illustrates a variable flow glaucoma shunt 200 ("shunt 200") configured in accordance with an embodiment of the present technology. The shunt 200 includes an inflow tube 210 fluidly connected to an outflow tube 220 (which can collectively be referred to as a "drainage element"). At least a portion of the inflow tube 210 is configured for placement within an anterior chamber in a region outside of the optical field of view of the eye. At least a portion of the outflow tube 220 is configured for placement within a desired outflow location, such as a sub-conjunctival bleb space. The shunt 200 further includes a flow control assembly 230 (also referred to herein as an "actuation assembly"). As will be described in greater detail below, the flow control assembly 230 is configured to act as a variable resistor to affect the amount of flow between the anterior chamber and the desired outflow location. In some embodiments, the shunt further includes an outer membrane 240 surrounding a portion of the outflow tube 220.

Figure 2B:
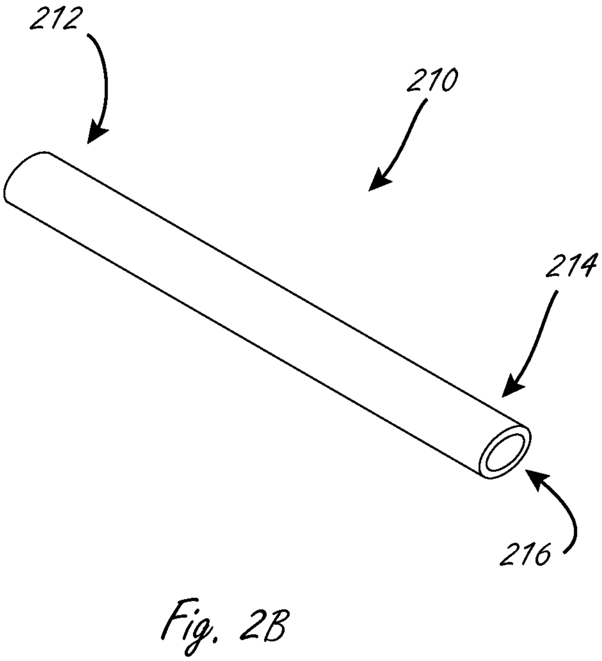

FIG. 2B illustrates the inflow tube 210 alone with the other portions of the shunt 200 (FIG. 2A) not shown for purposes of illustration. As best seen in FIG. 2B, the inflow tube 210 comprises a generally elongated tubular shape having a proximal end portion 212 and a distal end portion 214. A lumen 216 extends through the inflow tube 210 between the proximal end portion 212 and the distal end portion 214. The distal end portion 214 is configured for placement within the anterior chamber of an eye. For example, in some embodiments the distal end portion 214 is configured for placement within the anterior chamber in a space superior to the iris. The proximal end portion 212 is connectable to the outflow tube 220 such that the lumen 216 is fluidly connected to the outflow tube 220, described in greater detail with respect to FIG. 2C. When the shunt 200 is implanted in the eye, aqueous can enter the shunt 200 at the distal end portion 214 and flow towards the proximal end portion 212 via the lumen 216.

In some embodiments, the inflow tube 210 comprises an oval cross-sectional shape. An oval cross-sectional shape can minimize the height of the inflow tube 210 and thus can reduce the interaction of the inflow tube 210 and the corneal endothelium when the shunt 200 is implanted in the eye. In other embodiments, however, the inflow tube 210 has a substantially circular cross-sectional shape. In yet other embodiments, the inflow tube 210 has yet another cross-sectional shape, such as rectangular, pentagonal, etc. The inflow tube 210 can comprise any material suitable for placement within a human eye. In some embodiments, the inflow tube 210 is a flexible material such as silicone, urethane, etc. In some embodiments, the inflow tube 210 comprises a material known in the art to induce little to no inflammatory response.

Figure 2C:
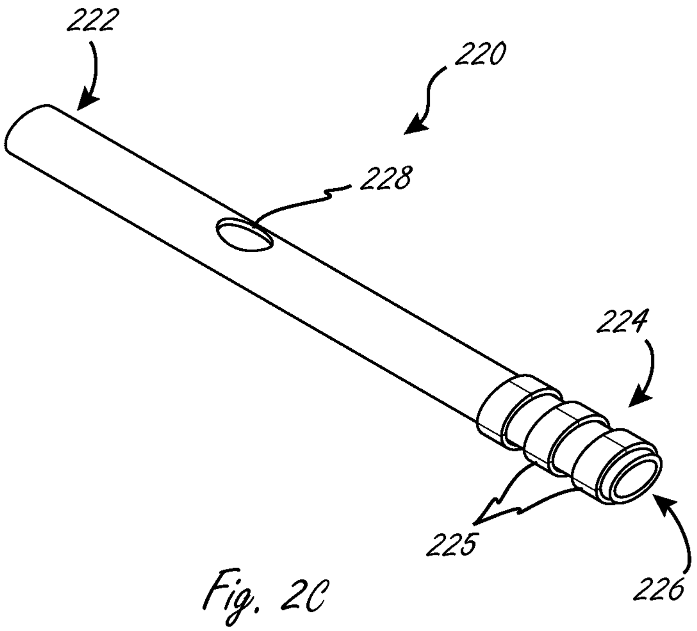

FIG. 2C illustrates the outflow tube 220 alone with the other portions of the shunt 200 (FIG. 2A) not shown for purposes of illustration. The outflow tube 220 comprises a generally elongated tubular shape having a proximal end portion 222 and a distal end portion 224. A lumen 226 extends through the outflow tube 220 between the proximal end portion 222 and the distal end portion 224. The distal end portion 224 of the outflow tube 220 is connectable to the proximal end portion 212 of the inflow tube 210 (FIGS. 2A and 2B). To facilitate this connection, the distal end portion 224 of the outflow tube 220 can include one or more retention features 225 that secure the outflow tube 220 to the inflow tube 210. The retention features 225 can include, for example, rings, barbs, cuts, and/or other elements known in the art for securing tubular elements together. In some embodiments, a portion of the outflow tube 220 overlaps with a portion of the inflow tube 210 when secured together. When the inflow tube 210 and the outflow tube 220 are secured together, the lumen 216 of the inflow tube 210 is fluidly connected to the lumen 226 of the outflow tube 220 to enable aqueous to flow from the lumen 216 to the lumen 226. In some embodiments, the outflow tube 220 comprises a rigid material that permits the flow control assembly 230 to slide along its outer surface, as described in greater detail below. Suitable materials for the outflow tube 220 include polyether ether ketone (PEEK), acrylic, polycarbonate, metal, ceramic, quartz, sapphire, composites thereof, and/or other rigid or semi-rigid materials known in the art. In some embodiments, the outflow tube 220 includes a coating (e.g., a biocompatible coating) that also confers one or more desired mechanical properties (e.g., rigidity).

The outflow tube 220 further includes an outflow hole or aperture 228 between the proximal end portion 222 and the distal end portion 224. The aperture 228 is in fluid communication with the lumen 226. Accordingly, as aqueous flows through the lumen 226, at least a portion of the aqueous will exit the lumen 226 via the aperture 228 unless the aperture 228 is covered by the flow control assembly 230, as described below with respect to FIGS. 2D and 2F. As one skilled in the art will appreciate from the disclosure herein, the outflow tube 220 can have a plurality of apertures 228 along its length and/or at the proximal end portion 222. Moreover, in some embodiments, the outflow tube 220 is integral with the inflow tube 210 to form a unitary tubular element. In such embodiments, the tube does not include retention features 225.

Figure 2D:
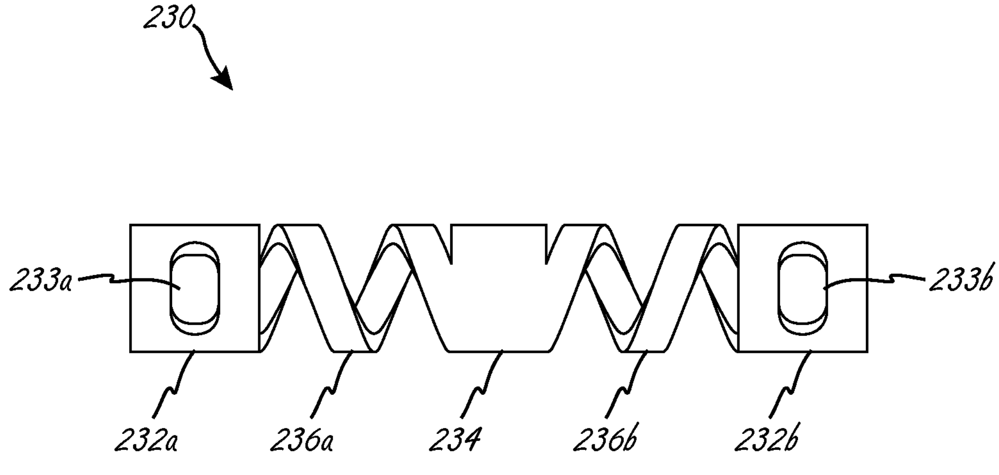

FIG. 2D is an enlarged view of the flow control assembly 230 with the other portions of the shunt 200 (FIG. 2A) not shown for purposes of illustration. The flow control assembly 230 includes a control element 234, a first anchoring element 232*a*, and a second anchoring element 232*b* (collectively referred to herein as "anchoring elements 232"). The first anchoring element 232*a* can include a first fixation hole 233*a* and the second anchoring element can include a second fixation hole 233*b* (collectively referred to herein as "fixation holes 233"). The control element 234 is connected to the first anchoring element 232*a* via a first actuation element 236*a* and to the second anchoring element 232*b* via a second actuation element 236*b*.

At least a portion of the flow control assembly 230 can be composed of a shape memory material (e.g., nitinol or another suitable shape memory material) capable of activation via energy, such as light and/or heat. For example, the first actuation element 236*a* and the second actuation element 236*b* can be composed of a shape memory material, such as a shape memory alloy (e.g., nitinol). Accordingly, the first actuation element 236*a* and the second actuation element 236*b* can be transitionable at least between a first material phase or state (e.g., a martensitic state, a R-phase, a composite state between martensitic and R-phase, etc.) and a second material phase or state (e.g., an austenitic state, an R-phase state, a composite state between austenitic and R-phase, etc.). In the first material state, the first actuation element 236*a* and the second actuation element 236*b* may be deformable (e.g., plastic, malleable, compressible, expandable, etc.). In the second material state, the first actuation element 236*a* and the second actuation element 236*b* may have a preference toward a specific preferred geometry (e.g., original geometry, manufactured geometry, heat set geometry, etc.). The first actuation element 236*a* and the second actuation element 236*b* can be transitioned between the first material state and the second material state by applying energy (e.g., heat) to the actuation elements to heat the actuation elements above a transition temperature. Energy can be applied to the actuation elements via an energy source positioned external to the body (e.g., a laser), RF heating, resistive heating, or the like. In some embodiments, the transition temperature for both the first actuation element 236*a* and the second actuation element 236*b* is above an average body temperature (e.g., an average temperature in the eye). Accordingly, both the first actuation element 236*a* and the second actuation element 236*b* are generally in the deformable first state when the shunt 200 is implanted in the body until they are actuated. If an actuation element (e.g., the first actuation element 236*a*) is deformed relative to its preferred geometry while in the first state, heating the actuation element (e.g., the first actuation element 236*a*) above its transition temperature causes the actuation element to transition to the second state and therefore move from the deformed shape to and/or toward its preferred geometry. In some embodiments, the first actuation element 236*a* can be selectively heated independently of the second actuation element 236*b*, and the second actuation element 236*b* can be selectively heated independently of the first actuation element 236*a*.

The first actuation element 236*a* and the second actuation element 236*b* generally act in opposition. For example, if the second actuation element 236*b* is deformed relative to its preferred geometry, actuation of the second actuation element 236*b* (e.g., heating the second actuation element 236*b* above its transition temperature) causes the second actuation element 236*b* to move toward its preferred geometry. This causes a corresponding deformation in the first actuation element 236*a*, which remains in the first material state and thus is generally malleable. For example, in the illustrated embodiment, the second actuation element 236*b* is compressed (e.g., shortened) relative to its preferred geometry. Heating the second actuation element 236*b* above its transition temperature causes the second actuation element 236*b* to straighten out (e.g., lengthen, expend, etc.) and move toward its preferred geometry. Because the second anchoring element 232*b* does not move as the second actuation element 236*b* changes shape, the first actuation element 236*a* (which is not heated and therefore in the first generally malleable state) is compressed to account for the shape change of the second actuation element 236*b*. This moves the control element 234 toward the first anchoring element 232*a*. The operation can be reversed by heating the first actuation element 236*a* above its transition temperature, which causes it to move (e.g., expand) toward its preferred geometry, which moves the control element 234 back toward the second anchoring element 232*b*. Accordingly, the first actuation element 236*a* and the second actuation element 236*b* can be selectively and independently actuated to toggle the control element 234 back and forth, which as described below can selectively block and/or unblock the aperture 228. Additional details regarding the operation of flow control assemblies generally similar to the flow control assembly 220 are described below in Section C and with reference to FIGS. 10A-10D.

In some embodiments, the flow control assembly 230 is cut from sheet or strip material. In such embodiments, each component of the flow control assembly comprises the same material, such as nitinol. To manufacture such nitinol-based flow control assemblies, the desired shape of the flow control assembly can be cut from a sheet or strip (e.g., a single sheet or a single strip) of nitinol. For example, substantially flat flow control assemblies can be laser cut from a single sheet or strip of nitinol material. Non-flat (e.g., spherical, cylindrical, conical, etc.) flow control assemblies (e.g., flow control assembly 230) can be laser cut from a single sheet of nitinol material and fused or otherwise formed into the desired non-flat configuration. However, as one skilled in the art will appreciate from the disclosure herein, the flow control assemblies can be formed using other suitable methods. For example, in embodiments in which the flow control assemblies are composed of nitinol, the flow control assemblies can be formed using any technique suitable for manipulating nitinol into the desired configuration.

In some embodiments, the first actuation element and/or the second actuation element (e.g., first actuation element 236*a* and/or second actuation element 236*b*) are optionally biased after forming the flow control assembly. For example, the first actuation element can be manipulated (e.g., using energy) such that it has a different length than the second actuation element upon attachment to the shunt/flow tube. Biasing at least one of the actuation elements before deployment of the shunt places the shunt in an "open" (e.g., permitting flow), partially "open", or "closed" (e.g., not permitting flow) position for the implant procedure. The biasing step can be done before or after attachment of the flow control assembly to the flow tube. The flow control assemblies can be secured to the shunt using anchoring techniques that hold the flow control assembly in the desired position and do not substantially interfere with operation of the shunt. For example, the flow control assembly (e.g., flow control assembly 230) can be secured to the flow tube (e.g., flow tube 220) via one or more anchoring elements (e.g., the first anchoring element 232*a* and/or the second anchoring element 232*b*). Once the flow control assembly is anchored to the flow tube, the flow tube 220 can be positioned within the outer membrane (e.g., outer membrane 2240) and secured in place using any suitable means.

Figure 2E:
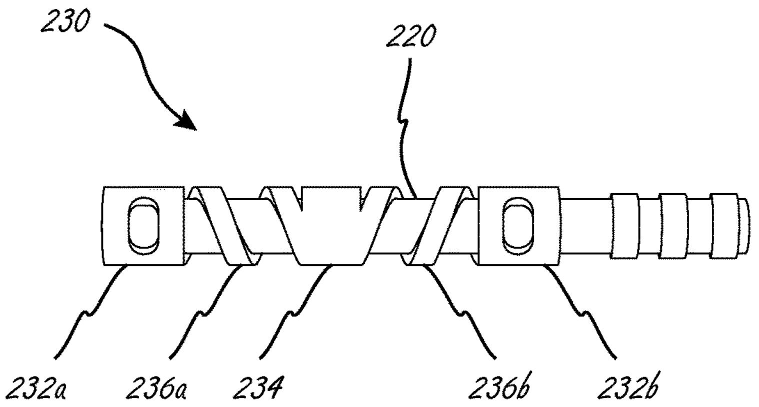
Figure 2F:
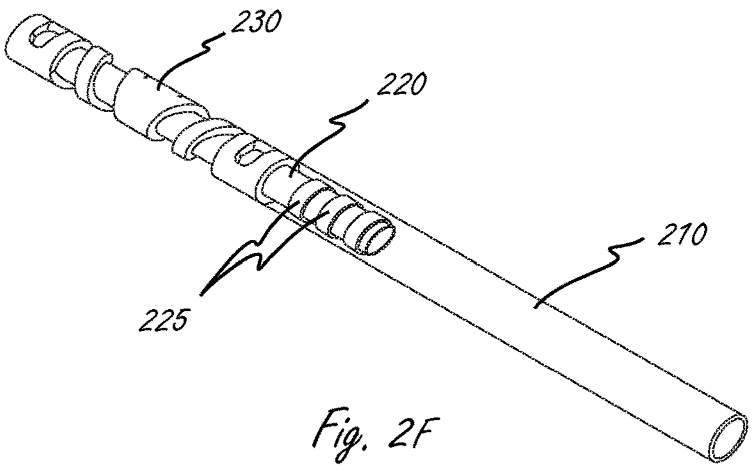

Referring to FIGS. 2E and 2F, the flow control assembly 230 is positionable around an outer circumference of the outflow tube 220. The anchoring elements 232 secure the flow control assembly 230 to the outflow tube 220. In some embodiments, for example, the fixation holes 233 can be used to connect the flow control assembly 230 to the outflow tube 220. In other embodiments, the fixation holes 233 can be omitted and the flow control assembly 230 may be secured to the outflow tube via other suitable means such as, for example, welding, epoxy, glue, and the like.

As described above, the actuation elements 236 are configured to slidably move (e.g., axially translate) the control element 234 back and forth along a length of the outflow tube 220 between the anchoring elements 232 For example, upon activation of at least one of the actuation elements 236, the control element 234 slidably moves along the outer surface of the outflow tube 220 in a first direction or a second direction, respectively, such that (a) the aperture 228 has a first fluid flow cross-section (e.g., completely open and accessible), or (b) the aperture 228 is at least partially covered by the control element 236 and has a second fluid-flow cross-section less than the first fluid flow cross-section (e.g., partially open/accessible). Further, in some instances the control element 236 may be slidably adjusted such that the aperture 228 is fully covered and inaccessible. The flow control assembly 230 can be selectively adjusted after placement within the eye (e.g., via an energy source positioned external to the eye) to provide a variety of different outflow resistance levels by incrementally adjusting the control element 236 relative to the aperture 228.

In some embodiments, the outflow tube 220 includes a plurality of apertures 228. In such embodiments, the flow control assembly 230 can be configured to move between a first position at least partially covering at least a first aperture and a second position not covering the first aperture. In some embodiments, movement of the flow control assembly 230 can be configured to at least partially cover or uncover more than just the first aperture. In some embodiments, at least one aperture 228 can remain at least partially uncovered at all times. In other embodiments, however, all of the apertures 228 can be covered by the flow control assembly 230 at the same time, depending on the positioning of the flow control assembly 230. The number of apertures 228 can be based at least in part on the desired aqueous drainage volume. Having a plurality of apertures 228 enables drainage of aqueous to continue even if one of the apertures 228 becomes blocked by tissue ingrowth or clotting.

Figure 2G:
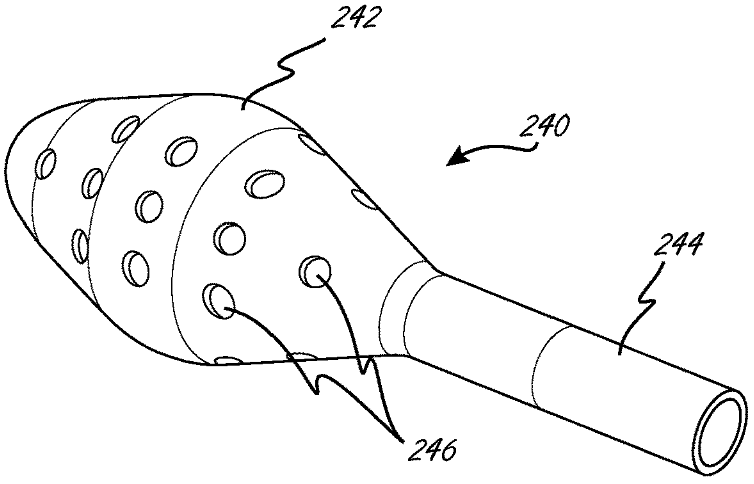

FIG. 2G illustrates the outer membrane 240 alone with the other portions of the shunt 200 (FIG. 2A) not shown for purposes of illustration. The outer membrane 240 can have a bladder portion 242 that encloses the flow control assembly 230 and a tubular portion 244 configured to receive a portion of the outflow tube 220 and/or the inflow tube 210. The bladder portion 242 can have a plurality of holes, slots, or channels 246 that allow aqueous to exit the membrane 240. The bladder portion 242 can comprise a variety of shapes, such as circular, oval, conical, etc. The outer membrane 240 can protect the flow control assembly 230 and permit the flow control assembly to move freely without interference from tissue. The outer membrane 240 can also keep a drainage bleb open by minimizing tissue ingrowth. In some embodiments, the outer membrane 240 can be configured to anchor the shunt 200 in a target position when the shunt 200 is implanted in an eye.

Figure 3A:
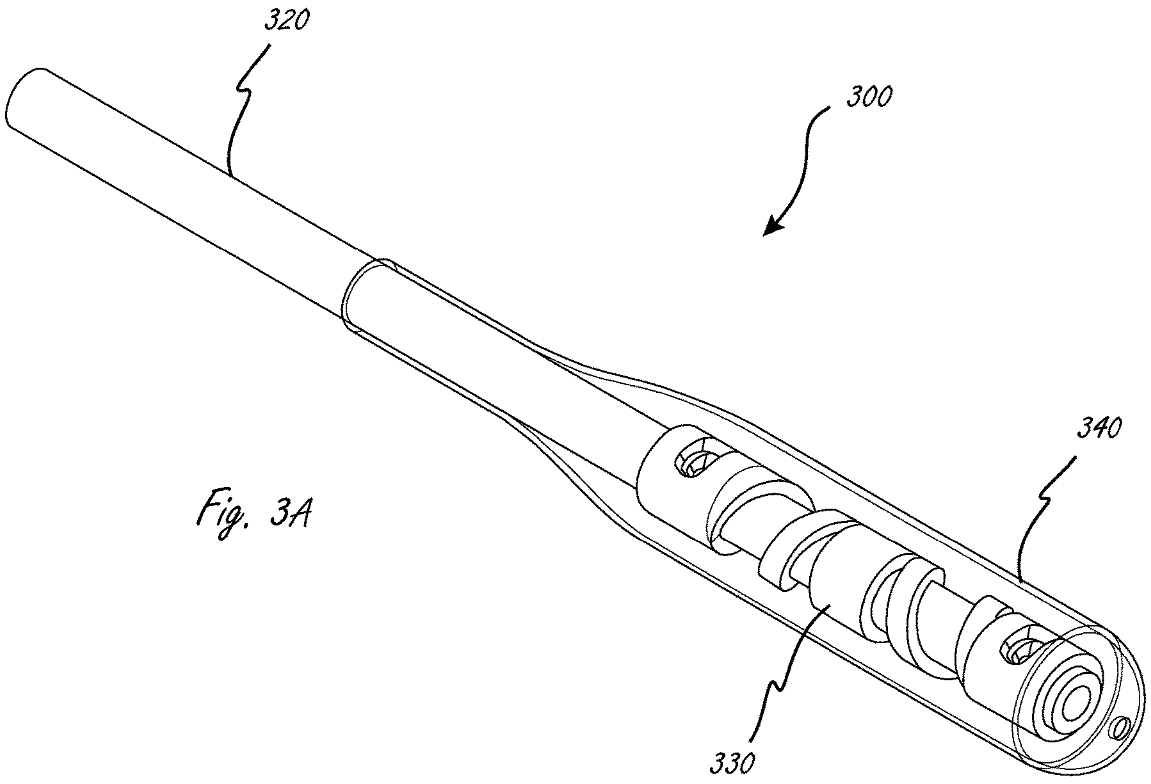
FIGS. 3A-3D illustrate an adjustable flow glaucoma shunt configured in accordance with another embodiment of the present technology.
Figure 3B:
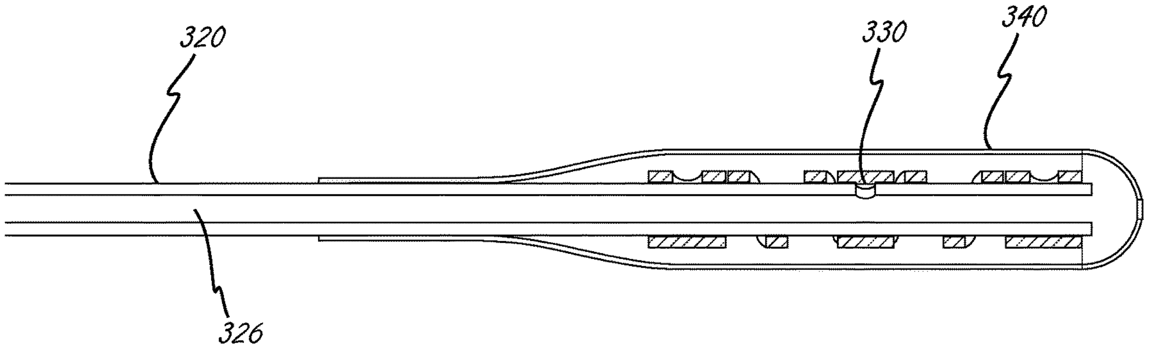
Figure 3C:
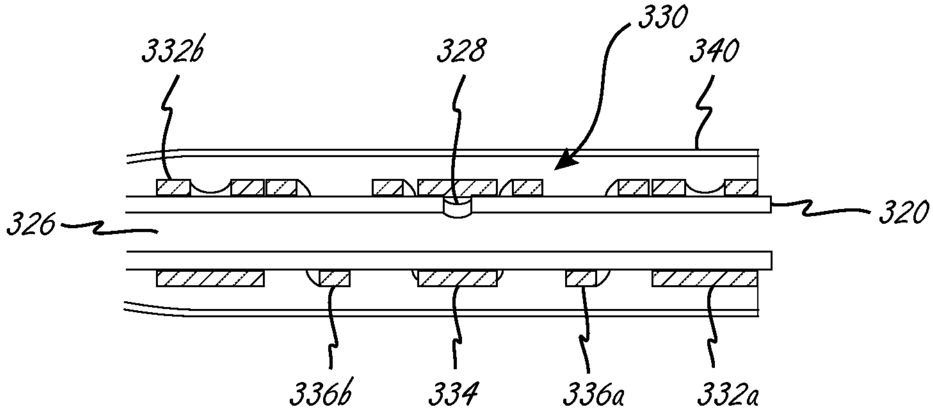

FIGS. 3A-3C illustrate a variable flow glaucoma shunt 300 ("shunt 300") configured in accordance with another embodiment of the present technology. The shunt 300 can include an outflow tube 320 having a lumen 326 extending therethrough, a flow control assembly 330, and an outer membrane 340. The outflow tube 320 can be connected to an inflow tube as described above with respect to FIGS. 2A-2G, or can comprise a single tubular element configured to extend between an anterior chamber and a drainage site when implanted in an eye. As described above with respect to FIGS. 2A-2G, the outflow tube 320 can comprise any material suitable for implanting into an eye. The outflow tube 320 can have a generally circular cross-section or can have an oval-shaped or other cross-sectional shape. When implanted into the eye, the outflow tube 320 enables aqueous to flow through the lumen 326.

The flow control assembly 330 can be substantially similar to the flow control assembly 230 described with respect to FIGS. 2A-2F. For example, as illustrated in FIG. 3C, which is a cross-sectional view of the flow control assembly 330 and the outflow tube 320, the flow control assembly 330 can include a first anchor 332*a*, a second anchor 332*b*, a first actuation element 336*a*, a second actuation element 336*b*, and a slidable control element 334 between the first actuation element 336*a* and the second actuation element 336*b*. As described above, the first actuation element 336*a* and the second actuation element 336*b* can be composed of a shape memory material, such as nitinol. Accordingly, the first actuation element 336*a* can be actuated (e.g. heated) to move (e.g., axially translate) the slidable control element 334 in a first direction, and the second actuation element 336*b* can be actuated (e.g., heated) to move the control element 334 in a second direction generally opposite the first direction. For example, as described in detail above with respect to the flow control assembly 230, applying energy to the first actuation element 336*a* can cause the first actuation element 336*a* to expand and push the slidable control element 334 towards the second anchor 332*b*. Applying energy to the second actuation element 336*b* causes the second actuation element 336*b* to expand and push the slidable control element 334 towards the first anchor 332*a*. Sliding the control element 334 along the length of the outflow tube can cover or uncover the aperture 328, thereby decreasing or increasing the amount of aqueous that can flow out of the outflow tube 320 via the aperture 328.

As illustrated in FIGS. 3A-3C, the outer membrane 340 can have a generally tubular volume having a generally circular or oval cross-sectional shape. The outer membrane 340 can include one or more outflow holes (not shown) that permit aqueous to flow out of the outer membrane 340 and into the bleb space the outer membrane 340 is positioned within. The outer membrane 340 can protect the flow control assembly 330 and permit the flow control assembly to move freely without interference from tissue. The outer membrane 340 can also keep a drainage bleb open by minimizing tissue ingrowth.

Figure 3D:
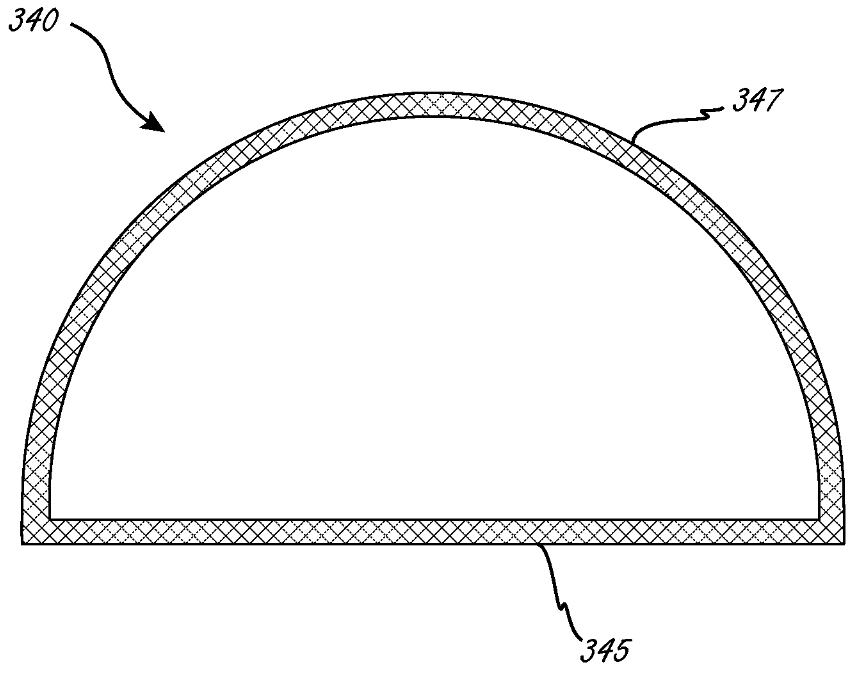

In some embodiments, the outer membrane 340 is dome-shaped. For example, FIG. 3D illustrates a cross-section of a dome-shaped outer membrane 340. As illustrated, the outer membrane 340 has a generally flat surface 345 and a generally semi-circular surface 347. In some embodiments, the height of the outer membrane 340 (e.g., the distance between the generally flat surface 345 and the generally semi-circular surface 347) is less than the width of the outer membrane 340. The generally flat surface 345 can help stabilize the shunt 300 when implanted in an eye. Additionally, the generally semi-circular surface 347 can reduce the surface-to-surface contact between the outer membrane 340 and the subconjunctiva when the shunt 300 is implanted in an eye. Without being bound by theory, this may reduce and/or prevent erosion of the subconjunctiva and/or the outer membrane 340. In addition, at least a portion of the outer membrane 340 can include a hydrophilic material or other weeping membrane to ensure the outer membrane 340 remains wetted. As one skilled in the art will appreciate from the disclosure herein, the outer membrane 340 can have other shapes, including non-round shapes (e.g., a "T" shape). Such embodiments, even if not explicitly described herein, are within the scope of the present technology. Shunts having non-round outer membranes can be delivered through needles with non-round cross-sections.

Figure 4A:
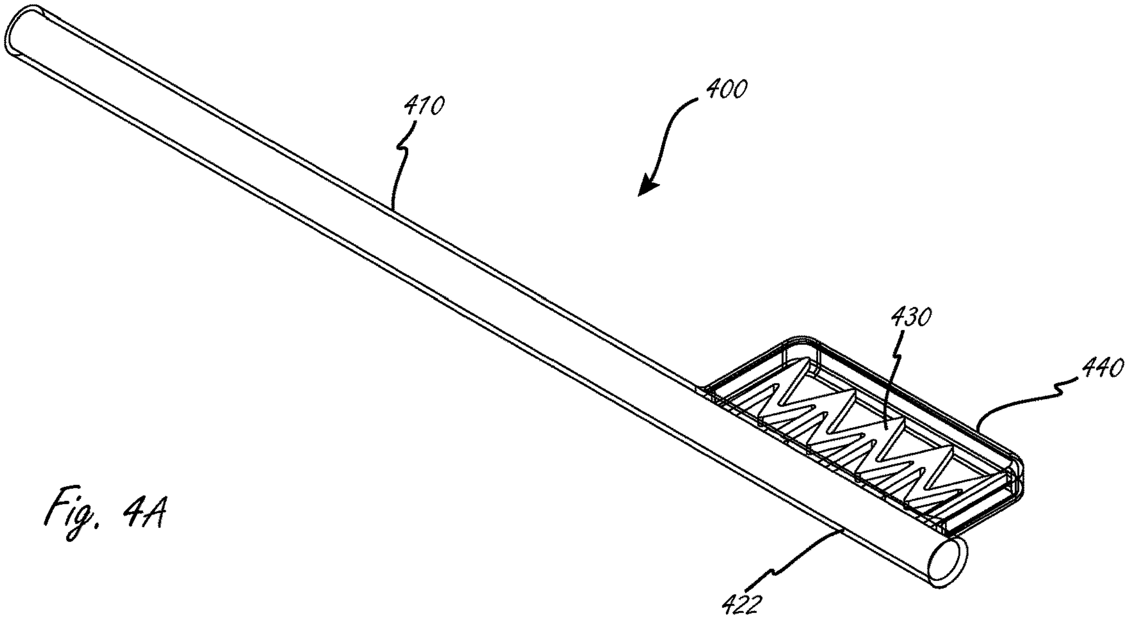
FIGS. 4A-4C illustrate an adjustable flow glaucoma shunt configured in accordance with yet another embodiment of the present technology.
Figure 4B:
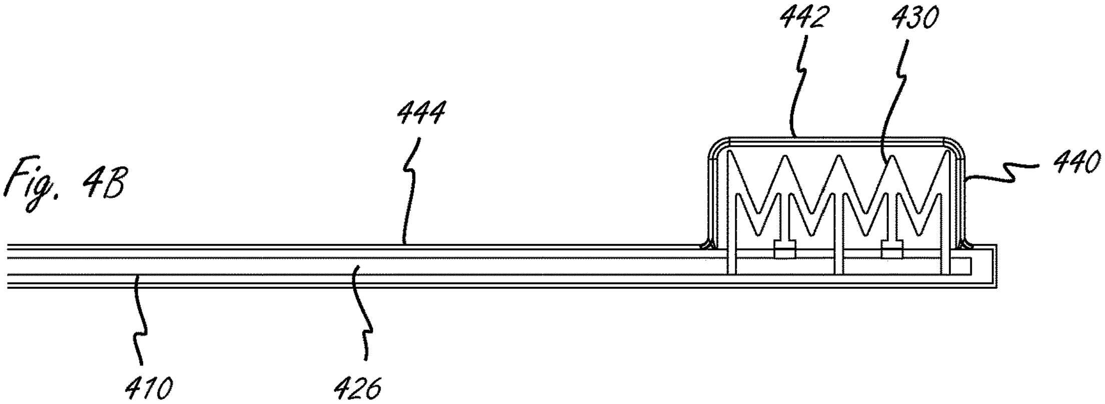
Figure 4C:
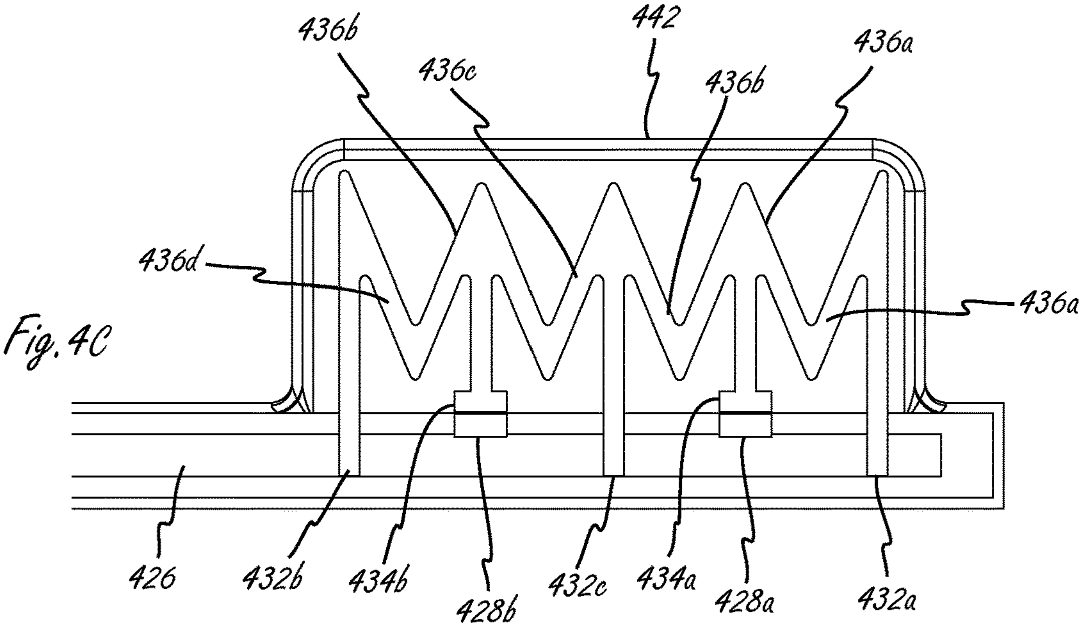

FIGS. 4A-4C illustrate yet another variable flow glaucoma shunt configured in accordance with an embodiment of the present technology. As illustrated, the variable flow glaucoma shunt 400 ("shunt 400") includes a flow tube 410, a flow control assembly 430, and an outer membrane 440. The flow tube 410 has a lumen 426 (FIGS. 4B and 4C) extending therethrough and is positionable between an anterior chamber of an eye and a subconjunctival bleb space. When implanted, the flow tube 410 can permit aqueous to flow through the lumen 426 to reduce a pressure in the anterior chamber. The tube can be a soft polymer-based material, a harder metallic-based material, or a hybrid. For example, in some embodiments the flow tube 410 includes an inflow tube coupled to an outflow tube, as described above with respect to FIGS. 2A-2G. In such embodiments, the inflow tube can comprise a soft polymer-based material and the outflow tube can comprise a harder metallic-based material. The flow tube 410 can include one or more apertures 428 (e.g., shown as a first aperture 428*a* and a second aperture 428*b* in FIG. 4C) positioned along a first end region 422 of the flow tube 410. The first end region 422 of the flow tube is positionable within a desired outflow location, such as a sub-conjunctival bleb space.

Referring to FIG. 4C, the flow control assembly 430 can include a first anchor portion 432*a*, a second anchor portion 432*b*, and a third anchor portion 432*c* (collectively referred to herein as "anchor portions 432"). The anchor portions 432 can secure the flow control assembly 430 to the outflow tube 410 without blocking the flow of aqueous through the lumen. The flow control assembly 430 further includes a first control element 434*a* configured to interface with (e.g., block) the first aperture 428*a* and a second control element 434*b* configured to interface with the second aperture 428*b*. The flow control assembly 420 includes a first actuation element 436*a* extending between the first anchor portion 432*a* and the first control element 434*a*, a second actuation element 436*b* extending between the third anchor portion 432*c* and the first control element 434*a*, a third actuation element 436*b* extending between the third anchor portion 432*c* and the second control element 434*b*, and a fourth actuation element 436*d* extending between the second anchor portion 432*b* and second control element 434*b*. The actuation elements 434*a-d* can be composed of a shape memory material and can operate in a manner generally similar to that described above with respect to the flow control assembly 230 of the shunt 200 (FIGS. 2A-2E). For example, the first actuation element 436*a* can be actuated to move the first control element 434*a* in a first direction, and the second actuation element 436*b* can be actuated to move the first control element 434*b* in a second direction generally opposite the first direction. Accordingly, the first actuation element 436*a* and the second actuation element 436*b* can be selectively actuated to move (e.g., axially slide) the first control element 434*a* back and forth, thereby changing the degree to which the first control element 434*a* blocks the first aperture 428*a* and the resistance through the first aperture 428*a*. Likewise, the third actuation element 436*c* can be actuated to move (e.g., axially slide) the second control element 434*b* in a first direction, and the fourth actuation element 436*d* can be actuated to move the second control element 434*b* in a second direction generally opposite the first direction. Accordingly, the third actuation element 436*c* and the fourth actuation element 436*d* can be selectively actuated to move the second control element 436*b* back and forth, thereby changing the degree to which the second control element 434*b* blocks the second aperture 428*b* and the resistance through the second aperture 428*b*. The first control element 434*a* and the second control element 434*b* can be moved back and forth independent of one another. Accordingly, the flow control assembly 430 can be selectively manipulated to achieve a desired flow rate of aqueous depending on the state of the patient.

Although the arrangement illustrated in FIGS. 4A-4C shows two apertures 428, two control elements 434, and four actuation elements 436*a-d*, it will be appreciated that in other embodiments the shunt 400 may have greater or fewer apertures, control elements, and/or actuation elements. For example, in some embodiments, the shunt 400 includes three apertures, three control elements, and six actuation elements. Further, the number of apertures, control elements, and actuation elements does not have to be equal. For example, in some embodiments, the shunt 400 may include four or more apertures, two control elements, and two actuation elements.

The shunt 400 includes an outer membrane 440 enclosing the flow control assembly 430 and at least a portion of the flow tube 410. The outer membrane 440 can include an enlarged bladder portion 442 configured to protect the flow control assembly 430 and a tubular portion 444 configured to encase at least a portion of the flow tube 410. The bladder portion 442 can have a plurality of holes, slots, or channels (not shown) that allow aqueous to exit the membrane 440. The outer membrane 440 can protect the flow control assembly 430 and permit the flow control assembly to move freely without interference from tissue. The outer membrane 440 can also keep a drainage bleb open. As illustrated, the outer membrane 440 can be substantially flat to minimize damage to the eye during and after implantation of the shunt 400. The outer membrane 440 may also help anchor the shunt 400 in a target location.

Figure 5A:
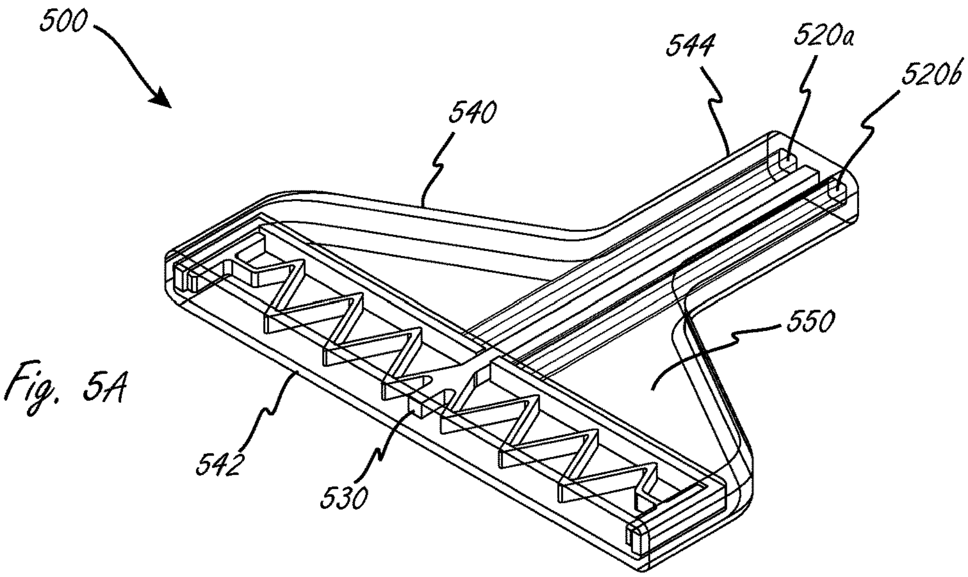
FIGS. 5A-5C illustrate an adjustable flow glaucoma shunt configured in accordance with yet another embodiment of the present technology.
Figure 5B:
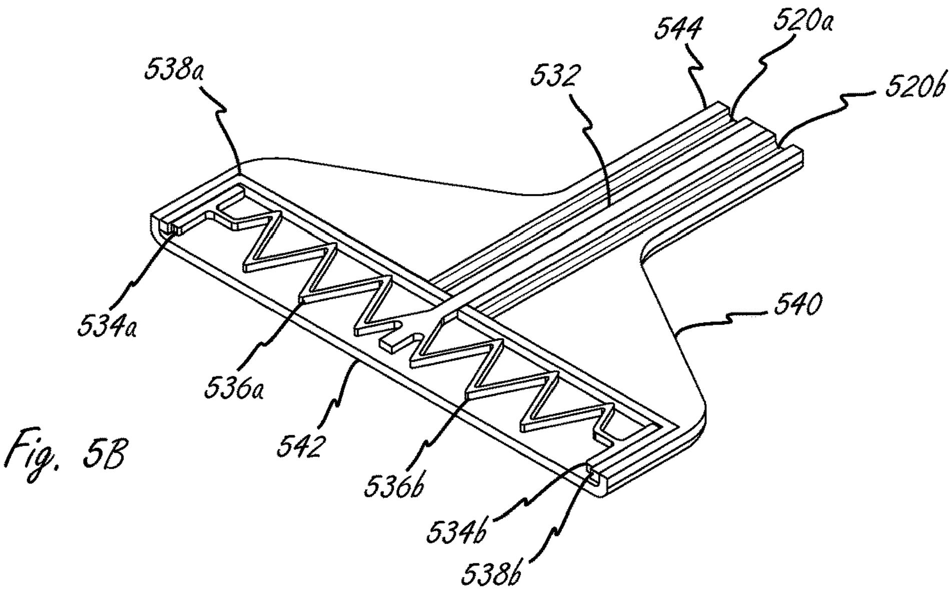
Figure 5C:
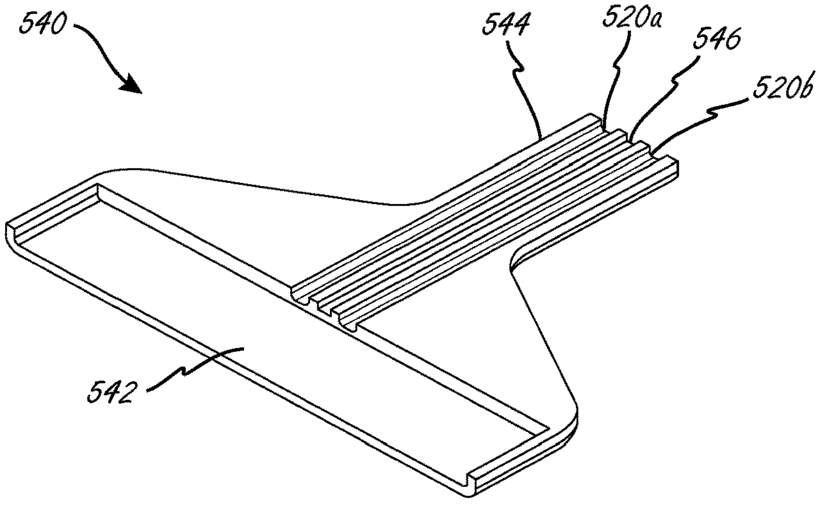

FIGS. 5A-5C illustrate yet another variable flow glaucoma shunt configured in accordance with select embodiments of the present technology. FIG. 5A is an isometric view of the variable flow glaucoma shunt ("shunt 500"), FIG. 5B is a cross-sectional view of the shunt 500, and FIG. 5C is a cross-sectional view of a shunt frame 540 with other features omitted for purposes of illustration.

The frame 540 includes a proximal portion 542 and a distal portion 544. The proximal portion 542 is configured to sit in the drainage space (e.g., in the bleb space) and the distal portion 544 is configured to penetrate through the sclera and into the anterior chamber. The shape of the frame 540 anchors the shunt 500 in position. In some embodiments, the frame 540 can be substantially flat (e.g., have a substantially flat profile with a thickness of about 100 μm or less, 90 μm or less, 80 μm or less, 70 μm or less, 60 μm or less, and/or 50 μm or less) to minimize damage to the eye during and after implantation of the shunt 500, while still being shaped to protect a flow control assembly 530 and anchor the shunt 500 in a target position. In addition to anchoring the shunt 500 and protecting the flow control assembly 530, the frame 540 can also define one or more flow channels that permit aqueous to flow from the anterior chamber towards the flow control assembly 530. For example, the illustrated embodiment includes a first flow channel 520*a* and a second flow channel 520*b* (collectively referred to herein as "flow channels 520"). In some embodiments, and as illustrated in FIG. 5A, the shunt 500 does not require an additional flow tube because the flow channels 520 facilitate aqueous drainage. However, in some embodiments, flow tubes (not shown) can be inserted into the flow channels 520. The frame 540 can also include a third channel 546 configured to receive an anchoring element 532 of the flow control assembly 530, described in greater detail below.

As provided above, the shunt 500 further includes the flow control assembly 530 carried by the frame 540. More specifically, the flow control assembly 530 can be positioned within the proximal portion 542 of the frame and configured to selectively control the flow of fluid through the flow channels 520. For example, the flow control assembly 530 includes a first control or gating element 538*a* configured to interface with (e.g., block) the first flow channel 520*a* and a second control or gating element 538*b* configured to interface with the second flow channel 520*b*. The first control element 538*a* and the second control element 538*b* can have a generally elbow or "L" shape. The flow control assembly 530 further includes a first actuation element 536*a* and a second actuation element 536*b*. The first actuation element 536*a* can extend between the anchoring element 532 and a first control element interfacing component 534*a*, which is configured to engage a portion of the first control element 538*a*. The second actuation element can extend between the anchoring element 532 and a second control element interfacing component 534*b*, which is configured to engage a portion of the second control element 538*b*. In some embodiments, the control gates 538*a*, 538*b* and the actuation elements 536*a*, 536*b* can be integrated into a single component laser cut from a nitinol sheet.

In the illustrated embodiment, the first control element 538*a* and the second control element 538*b* engage the anchoring element 532, although as described below the first and second control elements 538*a*, 538*b* can be selectively moved away from the anchoring element 532 via actuation of the first and second actuation elements 536*a*, 536*b*, respectively, to partially or fully unblock the first and second flow channels 520*a*, 520*b*, respectively. For example, the first actuation element 536*a* can selectively open or unblock the first flow channel 520*a*, and the second actuation element 536*b* can selectively open or unblock the second flow channel 520*b*. In some embodiments, the first actuation element 536*a* and the second actuation element 536*b* can be composed of a shape memory material and configured to operate substantially similar to the actuation elements previously described. For example, the first actuation element 536*a* may be compressed relative to its preferred geometry such that heating it above its transition temperature causes the first actuation element 536*a* to expand (e.g., lengthen), pushing (via the first control element interfacing component 534*a*) the first control element 538*a* away from the anchoring element 532 and unblocking (or at least partially unblocking) the first flow channel 520*a*. Likewise, the second actuation element 536*b* may be compressed relative to its preferred geometry such that heating it above its transition temperature causes the second actuation element 536*b* to expand (e.g., lengthen), pushing (via the second control element interfacing component 534*b*) the second control element 538*b* away from the anchoring element 532 and unblocking (or at least partially unblocking) the second flow channel 520*b*. The first and second actuation elements 536*a*, 536*b* can therefore be selectively actuated to modify the flow through the flow channels 520.

The shunt 500 can further include an outer membrane or cover 550 that encases the flow control assembly 530 and the frame 540, and which functions similarly to the outer membranes discussed above with respect to the shunts 300, 400, and 500. In some embodiments, the cover 550 can be substantially flat to minimize damage to the eye during and after implantation of the shunt 500, while still being shaped to protect a flow control assembly 530 and anchor the shunt 500 in a target position. The cover 550 can comprise a thin and flexible material to avoid excessive irritation of tissue.

Figure 6A:
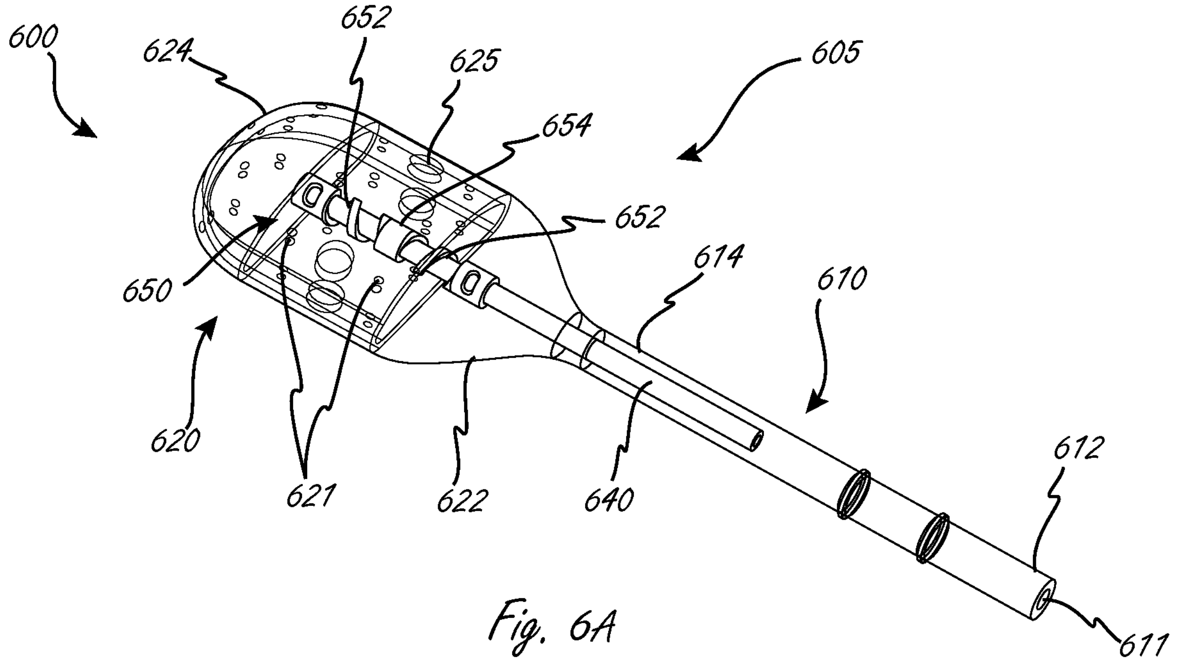
FIGS. 6A and 6B illustrate an adjustable flow glaucoma shunt configured in accordance with select embodiments of the present technology.

FIG. 6A is a partially transparent, isometric view of an adjustable shunt 600 ("shunt 600") configured in accordance with additional embodiments of the present technology. The shunt 600 includes an outer membrane 605, a flow tube 640, and a flow control assembly 650. The shunt 600 can be implanted in a human eye to fluidly connect an anterior chamber of an eye and a desired aqueous outflow location, such as a subconjunctival bleb space. Accordingly, the shunt 600 can be implanted in patients suffering from glaucoma to selectively increase the drainage of aqueous from the anterior chamber of the eye.

Figure 6B:
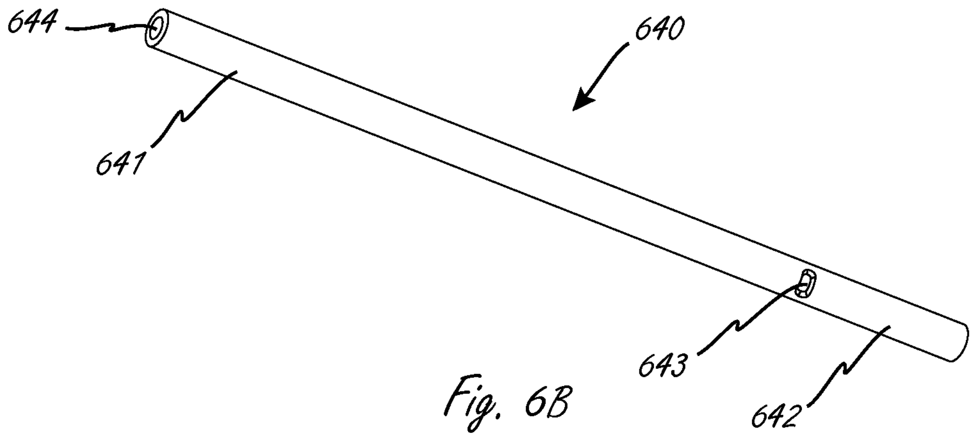

FIG. 6B illustrates the flow tube 640 alone with the other portions of the shunt 600 (FIG. 6A) not shown for purposes of illustration. The flow tube 640 comprises a generally elongated tubular shape having a proximal (e.g., upstream) end portion 641 and a distal (e.g., downstream) end portion 642. A lumen 644 extends through the flow tube 640 between the proximal end portion 641 and the distal end portion 642. The lumen 644 is configured to drain aqueous from the anterior chamber when the shunt 600 is implanted in the eye. For example, in some embodiments, the flow tube 640 extends from the anterior chamber to the target outflow location (e.g., bleb space). In such embodiments, the proximal end portion is positionable within an anterior chamber and the distal end portion is positionable within a drainage bleb. In other embodiments, the proximal end portion 641 of the flow tube 640 is not positioned within the anterior chamber, but instead is connectable to an inflow tube (not shown). The inflow tube can be configured for fluid communication with the anterior chamber. As previously described, having two distinct tubes permits the flow tube and inflow tube to be made of different materials, permitting different portions of the lumen path to have different properties (e.g., rigidity, flexibility, etc.). When the inflow tube and the flow tube 640 are secured together, the lumen 644 of the flow tube 640 is fluidly connected to a lumen of the inflow tube to enable aqueous to flow therethrough. In some embodiments, the flow tube 640 comprises a rigid material that permits the flow control assembly 650 to slide along its outer surface, as described in greater detail below. Suitable materials for the flow tube 640 include polyether ether ketone (PEEK), acrylic, polycarbonate, metal, ceramic, quartz, sapphire, and/or other rigid or semi-rigid materials known in the art. In some embodiments, the flow tube 640 includes a coating (e.g., a biocompatible coating) that also confers one or more desired mechanical properties (e.g., rigidity). In yet other embodiments, the shunt 600 does not include a flow tube. In such embodiments, the outer membrane 605 can define a lumen configured to be in fluid communication with the anterior chamber.

The flow tube 640 further includes an outflow hole or aperture 643 between the proximal end portion 641 and the distal end portion 642. The aperture 643 is in fluid communication with the lumen 644. Accordingly, as aqueous flows through the lumen 644, at least a portion of the aqueous will exit the lumen 644 via the aperture 643 unless the aperture 643 is covered (partially or completely) by the flow control assembly 650, as described below. As one skilled in the art will appreciate from the disclosure herein, the flow tube 640 can have a plurality of apertures 643 along its length and/or at the distal end portion 642.

The flow control assembly 650 can be generally similar to or the same as the flow control 230 described in detail with respect to FIGS. 2A-2G. For example, the flow control assembly 650 can include a plurality of actuation elements 652 configured to slidably move a control element 654 along a portion of the flow tube 640 to selectively block and/or unblock (or partially block and/or partially unblock) the aperture 643.

As best seen in FIG. 6A, the flow tube 640 and the flow control assembly 650 can be encased within the outer membrane 605. Accordingly, the outer membrane 605 can include an elongated (e.g., tubular) portion 610 and a bladder portion 620. The elongated portion 610 has a first portion or upstream portion 612, a second portion or downstream portion 614, and a lumen 611 extending therethrough. The lumen 611 can be configured to house at least a portion of the flow tube 640. The upstream portion 612 of the elongated portion 610 can be configured to reside within an anterior chamber of the eye when implanted. The elongated portion 610 can have a cross-sectional shape matching the cross-sectional shape of the flow tube 640. For example, if the flow tube 640 has an oval-shaped cross-section, the elongated portion 610 can have an oval-shaped cross-section. This is expected to minimize the overall profile of the elongated portion 640 while still providing protection to and/or encasing the flow tube 640.

The bladder portion 620 can encase the flow control assembly 650 and the distal end portion of the flow tube 640. The bladder portion 620 can include a plurality of apertures 621 configured to fluidly connect an interior chamber defined by the bladder portion 620 and an environment external to the bladder portion 620. Accordingly, when implanted within the eye, the bladder portion 620 can be configured to reside within a target outflow location, such as a subconjunctival bleb space. The apertures 621 permit aqueous draining through the aperture 643 of the flow tube 640 to exit the interior chamber of the bladder portion 620 and flow into the bleb space. In some embodiments, the apertures 621 are positioned at a distal end portion of the bladder portion 620. A proximal end portion 622 of the bladder 620 adjacent the elongated portion 612 can be generally free from apertures. Without being bound by theory, the foregoing placement of apertures along the bladder portion 620 is expected to improve the drainage characteristics of the shunt 600, as described in detail below with respect to FIGS. 8A and 8B. The bladder portion 620 can also include one or more attachment mechanisms configured to secure the shunt 600 in a desired position. In the illustrated embodiment, the bladder portion 620 includes a plurality of suture holes 625. The suture holes enable the bladder portion to be secured to adjacent tissue and therefore help secure the shunt 600 in a desired position.

The bladder portion 620 can serve a number of functions. First, the bladder portion 620 can protect the flow control assembly 650 and permit the flow control assembly 650 to move freely without interference from tissue. Second, the shape of the bladder portion 620 can help anchor the shunt 600 in a target position when the shunt 600 is implanted in an eye, and/or the bladder portion 620 can include additional anchoring features (e.g. suture holes, ribs, wings, etc.). This can be especially beneficial in the first few days or weeks following implantation before tissue ingrowth into the shunt 600 has occurred. Third, the bladder portion 620 can help keep a drainage bleb open by minimizing tissue ingrowth into the drainage space surrounding the outflow end of the flow tube 640. Fourth, the bladder portion 620 can reduce a backflow pressure through the flow tube 640. Reducing the backflow pressure through the flow tube can help maintain drainage of aqueous through the flow tube, even in embodiments without a flow control assembly 650.

Although shunt 600 is described as having the flow control assembly 650 positionable at or adjacent an outflow end of the shunt, the flow control assemblies described herein can also be positioned at other positions along the length of the shunt. For example, the flow control assembly 650 can be positioned near a proximate (e.g., inflow) end of the shunt and/or within an anterior chamber. Accordingly, shunt 600 can be oriented in multiple directions, depending on the desired arrangement (e.g., the shunt 600 can be implanted with the flow control assembly proximate the anterior chamber or with the flow control assembly proximate the desired outflow location). In some embodiments, placing the flow control assembly 650 in the anterior chamber is expected to reduce the amount of tissue interference with the non-invasive energy used to selectively adjust the flow control assembly. In embodiments in which the flow control assembly 650 is positioned within the anterior chamber, the bladder portion 620 of the outer membrane 605 can also be positioned within the anterior chamber. When placed in the anterior chamber, the bladder portion 620 can serve several similar functions to those described above. For example, the bladder portion 620 can protect the flow control assembly and/or anchor the shunt. If the bladder portion 620 is positioned around the flow control assembly 650 in the anterior chamber, the shunt 620 can optionally have a second bladder (not shown) surrounding the outflow end of the shunt. The second bladder can reduce backflow pressure through the shunt and/or help prevent tissue ingrowth in a bleb or other desired outflow location.

Additional aspects of outer membranes/covers for adjustable shunts, such as outer membrane 605, are described below with respect to FIGS. 7A-9. As one skilled in the art will appreciate, however, the following embodiments are not limited to use with shunt 600, but rather can be readily adapted for use with a variety of other adjustable glaucoma shunts described above with reference to FIGS. 2A-6B and other suitable shunts. Moreover, discussion of certain features is omitted from the following description to avoid obscuring certain other features. However, any of the features described herein can be combined in any manner to form adjustable shunts and/or outer membranes for adjustable shunts in accordance with the present technology.

Figure 7A:
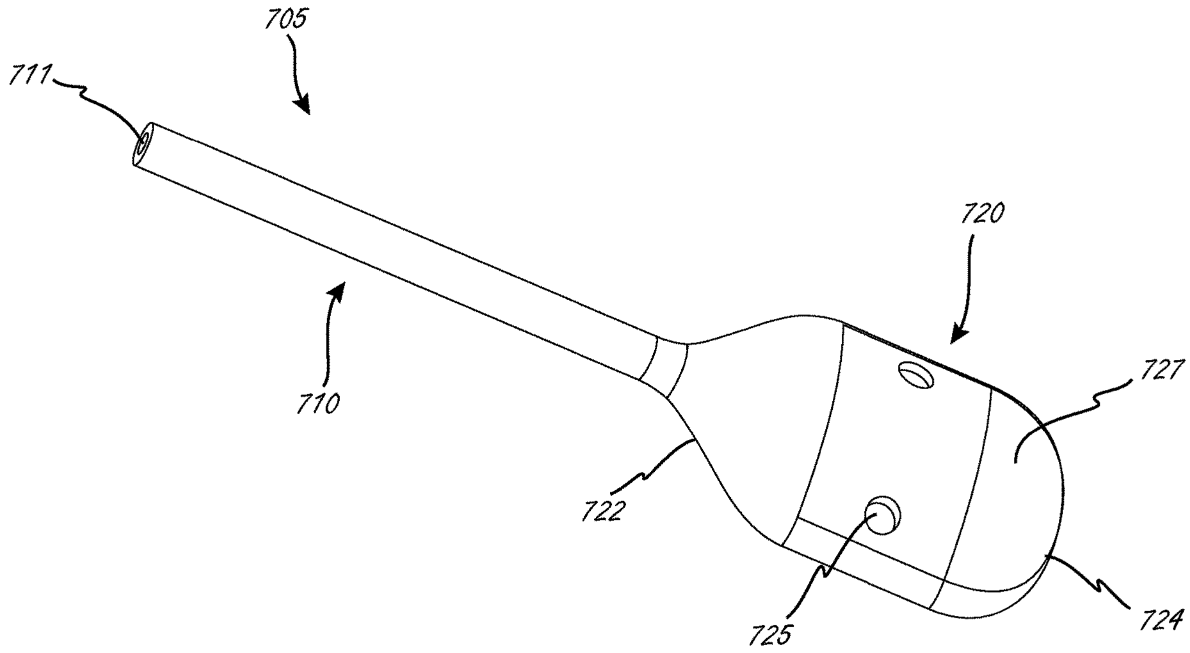
FIGS. 7A and 7B illustrate an outer membrane of an adjustable flow glaucoma shunt configured in accordance with select embodiments of the present technology.

FIG. 7A, for example, illustrates an outer membrane 705 for use with an adjustable glaucoma shunt configured in accordance with select embodiments of the present technology. As described above with respect to outer membrane 605 in FIG. 6A, the outer membrane 705 can include an elongated tubular portion 710 configured to encase at least a portion of a flow tube and a bladder portion 720 configured to encase a flow control assembly and a downstream portion of the flow tube. Accordingly, the elongated portion 710 can define a lumen 711 configured to house a portion of the flow tube, and the bladder portion 720 can define an interior chamber that houses the flow control assembly and the downstream portion of the flow tube. The bladder portion 720 can include an upstream portion 722, a downstream portion 724, and a first surface 727 extending between the upstream portion 722 and the downstream portion 724. The bladder portion 720 can also have one or more attachment mechanisms, such as suture holes 725, configured to secure a shunt (e.g., shunt 600) in a desired position.

Figure 7B:
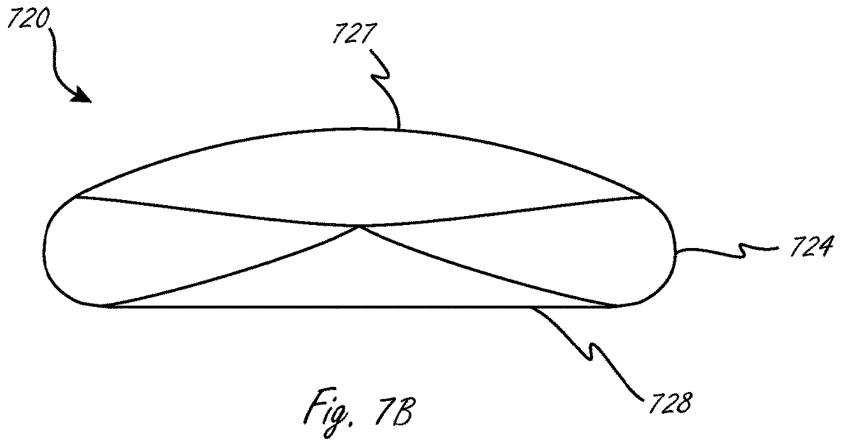

FIG. 7B is a front view of the distal end portion 724 of the bladder portion 720. As illustrated, the bladder portion 720 can have a generally dome-shaped and/or D-shaped configuration having a generally curved first surface 727 and a generally flat second surface 728. In some embodiments, the height of the bladder portion 720 (e.g., the distance between the generally curved first surface 727 and the generally flat second surface 728) is less than the width of the bladder portion 720. In some embodiments, the width is generally greater than the height to minimize damage to the eye while maximizing stabilization of the implanted shunt. For example, a ratio between the width and the height of the bladder portion 720 can be between about 2.5:1 and 1.2:1, although other ratios are possible. The generally flat second surface 728 can help stabilize the shunt when implanted in an eye. In some embodiments, the generally flat second surface 728 can be textured to help reduce lateral or axially migration of the shunt. Additionally, the generally curved first surface 727 can reduce the surface-to-surface contact between the outer membrane 705 and the subconjunctiva when implanted in an eye. This may reduce and/or prevent erosion of the subconjunctiva. In addition, at least a portion of the outer membrane 705 can include a hydrophilic material or other weeping membrane to ensure the outer membrane 705 remains wetted. As one skilled in the art will appreciate from the disclosure herein, the outer membrane 705 can have other shapes, including round and non-round shapes (e.g., a "T" shape). Such embodiments, even if not explicitly described herein, are within the scope of the present technology. Shunts having non-round outer membranes can be delivered through needles with non-round cross-sections. In other embodiments, shunts having non-round outer membranes can be rolled to have a generally round cross-section such that they can be delivered via needles having a round cross-section. In such embodiments, the non-round outer membranes are configured to unfurl into their expanded configuration upon deployment of the shunt in the eye.

Figure 8A:
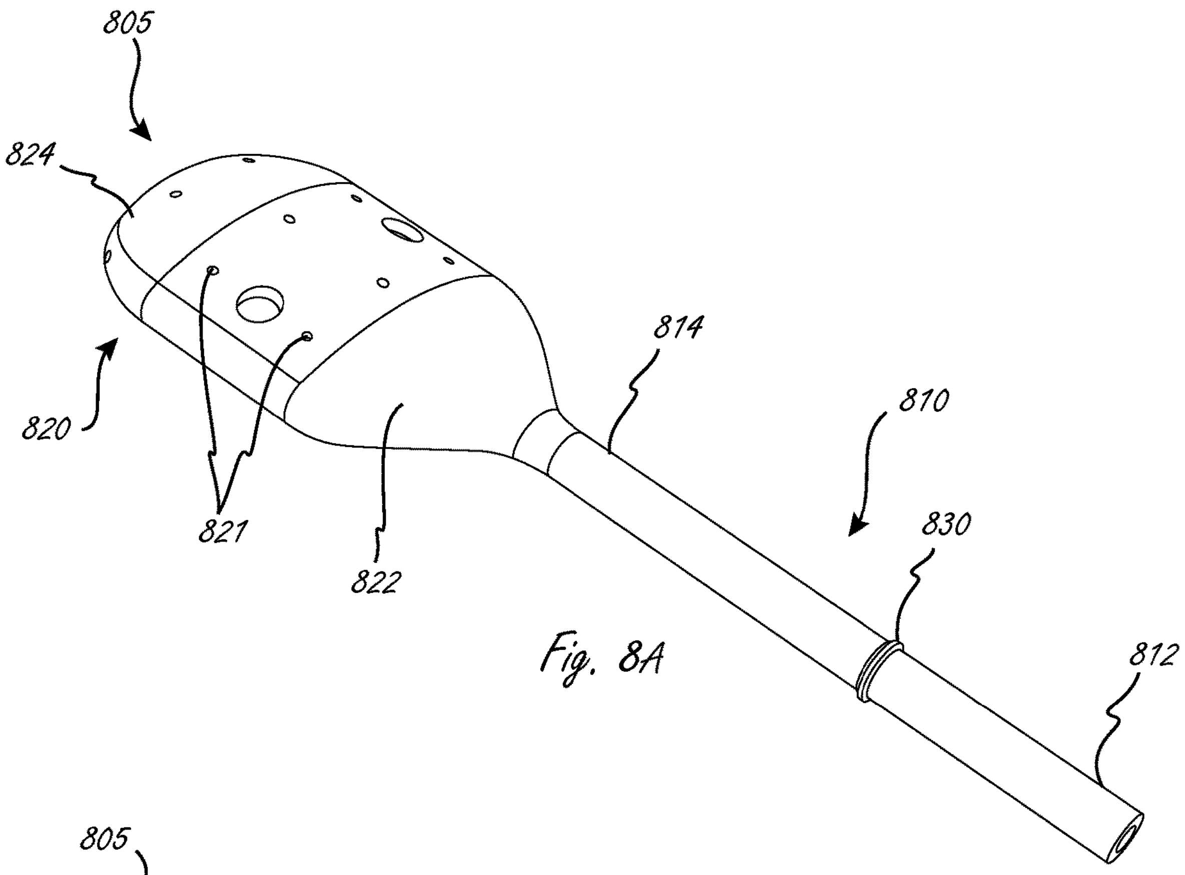
FIGS. 8A and 8B illustrate additional aspects of an outer membrane of an adjustable flow glaucoma shunt configured in accordance with select embodiments of the present technology.
Figure 8B:
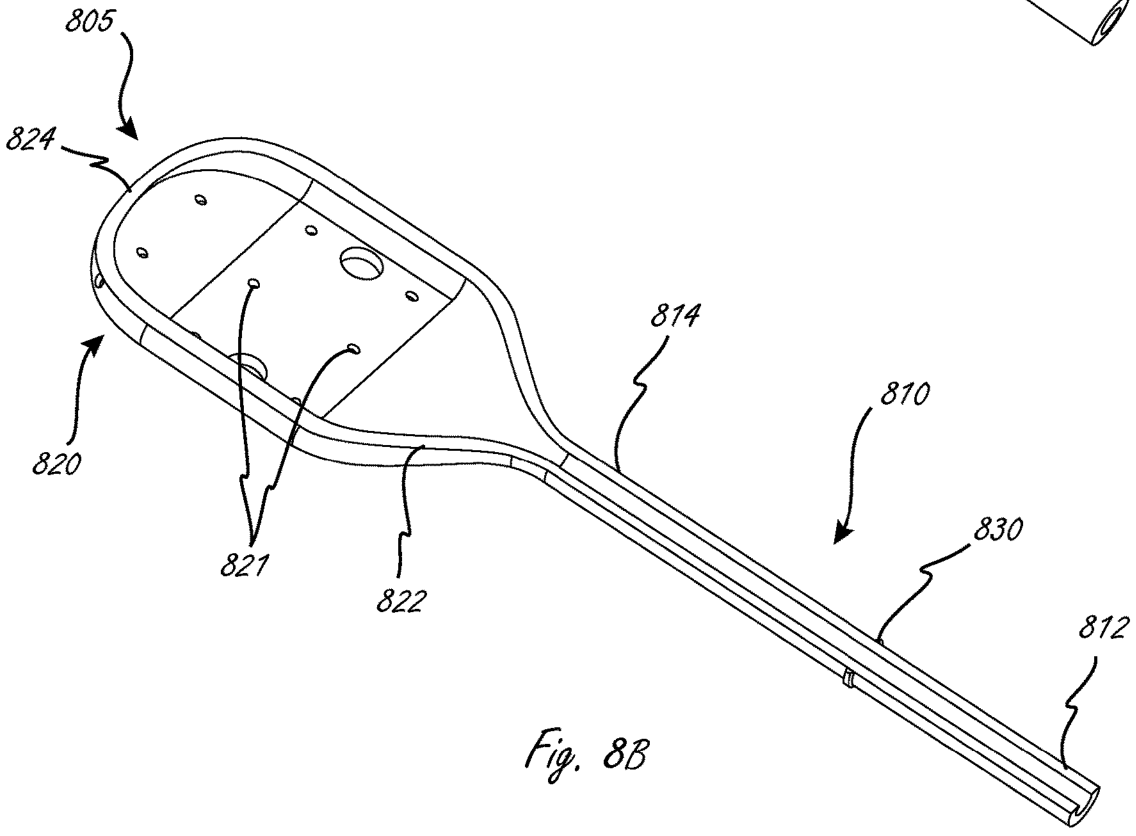

FIGS. 8A and 8B illustrate additional aspects of an outer membrane 805 for use with adjustable shunts disclosed herein and configured in accordance with select embodiments of the present technology. More specifically, FIG. 8A is an isometric view of the outer membrane 805 and FIG. 8B is an isometric view of the outer membrane 805 with an upper portion of the membrane removed for purposes of illustration. The outer membrane 805 can be generally similar to the outer membranes 605 and 705, with the following additional features. In particular, the outer membrane 805 includes a ring 830 on its elongated tubular portion 810. The ring 830 is positioned between the proximal end portion 812 and the distal end portion 814 of the elongated tubular portion 810. The ring 830 can help locate the shunt in the eye during implantation. For example, the shunt can be advanced until the ring 830 is pressed up against the point at which the shunt tunnels through the sclera and enters the anterior chamber. This defines the location of the shunt in the eye. Once implanted, the ring 830 helps prevent axial translation of the shunt, preventing migration of the shunt further into the anterior chamber.

The outer membrane 805 also includes a plurality of apertures 821 on the bladder portion 820. As described above, the apertures 821 permit aqueous to drain from an interior chamber defined by the bladder portion into the surrounding environment (e.g., the bleb space). As illustrated, the plurality of apertures 821 are positioned on a medial and distal portion 824 of the bladder portion 820. There are no apertures on the proximal portion 822. Such a configuration pushes aqueous draining through the apertures 821 away from the globe of eye and ensures any growth in the drainage bleb will also be away from the globe of the eye.

Figure 9:
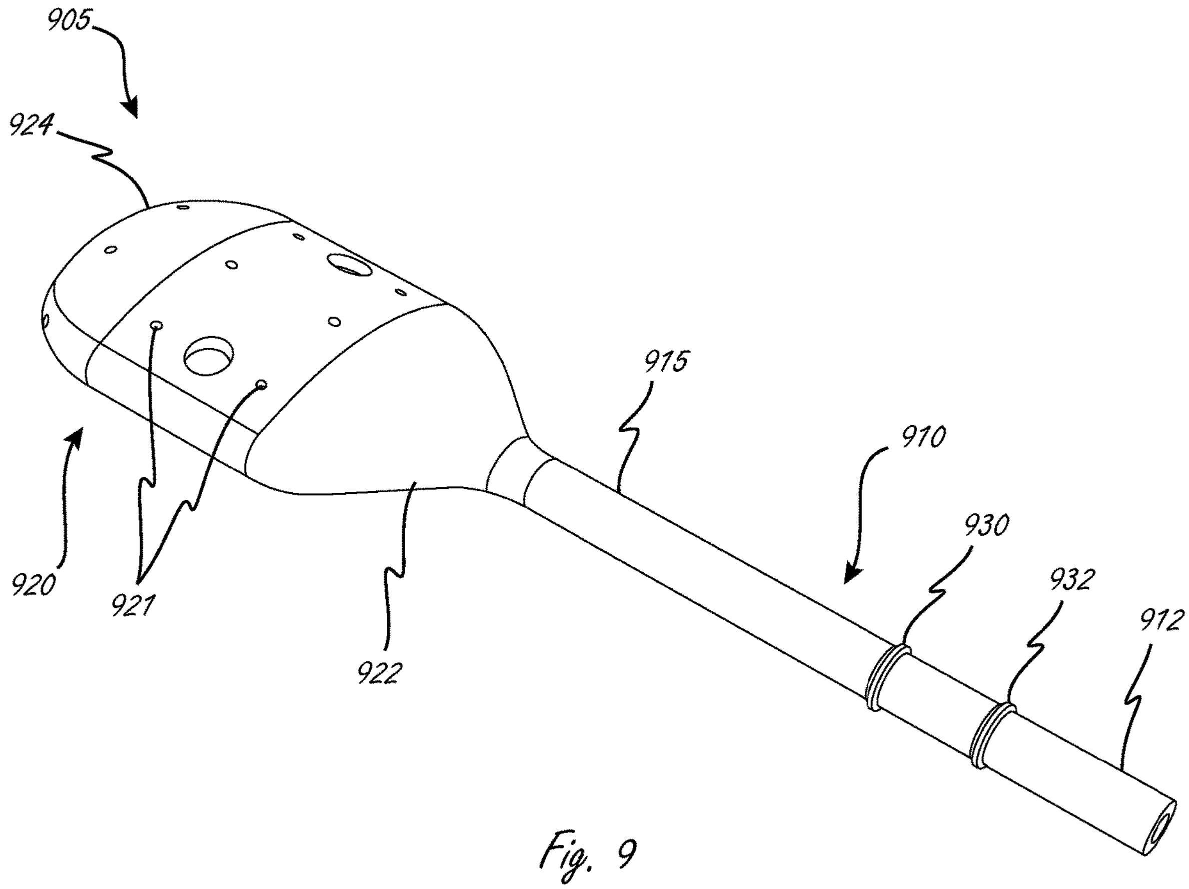
FIG. 9 illustrates additional aspects of an outer membrane of an adjustable flow glaucoma shut and configured in accordance with select embodiments of the present technology.

FIG. 9 is a schematic illustration of additional aspects of an outer membrane 905 for use with adjustable shunts disclosed herein and configured in accordance with select embodiments of the present technology. The outer membrane 905 can be generally similar to outer membranes 605, 705, and 805, with the following additional features. Instead of having a single ring, outer membrane 905 includes a first ring 930 and a second ring 932 on the tubular portion 910. The first ring 930 and the second ring 932 are positioned between the proximal end portion 912 and the distal end portion 914 of the tubular portion 910. The first ring 930 functions similarly to ring 830 described above with respect to FIGS. 8A and 8B. The second ring 932 can be positionable within the anterior chamber. This further secures the shunt in a desired target location and further reduces axial migration of the shunt. To facilitate delivery, the second ring 932 can be flush with the tubular portion 910 (e.g., the second ring 932 has the same diameter as the tubular portion 910) during deployment of the device. After the second ring 932 is positioned in the anterior chamber, it can be expanded into the illustrated configuration. The second ring 932 could be expanded via mechanical and/or remote actuation (e.g., energy).

As one skilled in the art will appreciate, adjustable shunts configured in accordance with the present technology can include any combination of the above described features and are not limited to the specific embodiments illustrated herein. Moreover, although the shunts discussed above are primarily described as having the flow control assembly positioned at or adjacent an outflow end of the shunt, the flow control assemblies described herein can also be positioned at other positions along the length of the shunt. For example, the flow control assembly can be positioned near a proximate (e.g., inflow) end of the shunt and/or within an anterior chamber. Accordingly, the shunts described above in FIGS. 2A-9 can be oriented in multiple directions, depending on the desired arrangement (e.g., the shunts can be implanted with the flow control assembly proximate the anterior chamber or with the flow control assembly proximate the desired outflow location). In some embodiments, placing the flow control assembly in the anterior chamber is expected to reduce the amount of tissue interference with the non-invasive energy used to selectively adjust the flow control assembly. In embodiments in which the flow control assembly is positioned within the anterior chamber, the bladder portion of the outer membrane can also be positioned within the anterior chamber. When placed in the anterior chamber, the bladder portion can serve several similar functions to those described above. For example, the bladder portion can protect the flow control assembly and/or anchor the shunt. If the bladder portion is positioned around the flow control assembly in the anterior chamber, the shunts described herein can optionally have a second bladder surrounding the outflow end of the shunt. The second bladder can reduce backflow pressure through the shunt and/or help prevent tissue ingrowth in a bleb or other desired outflow location.

In many of the embodiments described herein, the flow control assemblies are configured to introduce features that selectively impede or attenuate fluid flow through the shunt during operation. In this way, the flow control assemblies can incrementally or continuously change the flow resistance through the shunt to selectively regulate pressure and/or flow. The flow control assemblies configured in accordance with the present technology can accordingly adjust the level of interference or compression between a number of different positions, and accommodate a multitude of variables (e.g., TOP, aqueous production rate, native aqueous outflow resistance, and/or native aqueous outflow rate) to precisely regulate flow rate through the shunt.

The disclosed flow control assemblies can be operated using energy. This feature allows such devices to be implanted in the patient and then modified/adjusted over time without further invasive surgeries or procedures for the patient. Further, because the devices disclosed herein may be actuated via energy, such devices do not require any additional power to maintain a desired orientation or position. Rather, the actuators/fluid resistors disclosed herein can maintain a desired position/orientation without power. This can significantly increase the usable lifetime of such devices and enable such devices to be effective long after the initial implantation procedure.

The shunts described herein can be implanted having a first drainage rate and subsequently remotely adjusted to achieve a second drainage rate. The adjustment can be based on the needs of the individual patient. For example, the shunt may be implanted at a first lower flow rate and subsequently adjusted to a second higher flow rate once inflammation reduces. The shunts described herein can be delivered using either ab interno or ab externo implant techniques, and can be delivered via needles. The needles can have a variety of shapes and configurations to accommodate the various shapes of the shunts described herein. For example, in some embodiments, the needles may be hinged to facilitate implantation through the sclera. Details of the implant procedure, the implant devices, and bleb formation are described in greater detail in PCT Patent Application No. PCT/US20/41152, titled "MINIMALLY INVASIVE BLEB FORMATION DEVICES AND METHODS FOR USING SUCH DEVICES," filed Jul. 8, 2020, the disclosure of which is hereby incorporated by reference herein for all purposes.

Aspects of the present technology are further directed to methods of manufacturing the shunts described herein. As described herein, for example, select embodiments of the present technology include a flow control assembly composed, at least in part, of nitinol. To manufacture such nitinol-based flow control assemblies, the desired shape of the flow control assembly can be cut from a sheet or strip of nitinol. For example, substantially flat flow control assemblies (e.g., flow control assemblies 430 and 530 of shunts 400 and 500) can be laser cut from a single sheet or strip of nitinol material. Non-flat (e.g., spherical, cylindrical, conical, etc.) flow control assemblies (e.g., flow control assemblies 230 and 330 of shunts 200 and 300) can be laser cut from a single sheet or strip of nitinol material and fused or otherwise formed into the desired non-flat configuration. However, as one skilled in the art will appreciate from the disclosure herein, the flow control assemblies can be formed using other suitable methods. For example, in embodiments wherein the flow control assemblies comprise nitinol, the flow control assemblies can be formed using any technique suitable for manipulating nitinol into the desired configuration. As one skilled in the art will appreciate from the disclosure herein, the present technology is not limited to the methods of manufacture expressly described herein. Rather, the shunts described herein can be manufactured using other suitable methods not expressly set forth herein.

C. Operation of Shape Memory Actuation Elements

As discussed above, the present technology is generally directed to implantable systems and devices for facilitating the flow of fluid between a first body region and a second body region. The devices generally include a drainage and/or shunting element having a lumen extending therethrough for draining or otherwise shunting fluid between the first and second body regions. Further, devices configured in accordance with the present technology may be selectively adjustable to control the amount of fluid flowing between the first and second body regions. In some embodiments, for example, the devices comprise an actuation assembly that drives movement of a flow control element to modulate flow resistance through the lumen, thereby increasing or decreasing the relative drainage rate of fluid between the first body region and the second body region.

In some embodiments of the present technology, the flow control assemblies (e.g., actuation assemblies, flow control mechanisms, fluid resistors, etc.) comprise at least two actuation elements coupled to a moveable element (e.g., a control element, a gating element, an arm, etc.). The moveable element can be formed to interface with (e.g., at least partially block) a corresponding port, such as a lumen orifice. The port can be an inflow port or an outflow port. In other embodiments, the moveable element can be an intermediate element between the actuation element and a flow control element that interfaces with or otherwise engages a shunt lumen or orifice. In such embodiments, movement of the moveable element can adjust a geometry of the flow control element, which in turn adjusts a size, shape, or other dimension of a shunt lumen or orifice. Movement of the actuation elements generates (e.g., translational and/or rotational) movement of the moveable element.

The actuation element(s) can include a shape memory material (e.g., a shape memory alloy, or a shape memory polymer). Movement of the actuation element(s) can be generated through applied stress and/or use of a shape memory effect (e.g., as driven by a change in temperature). The shape memory effect enables deformations that have altered an element from its preferred geometric configuration (e.g., original configuration, shape-set configuration, heat-set configuration, etc.) to be largely or entirely reversed during operation of the flow control assembly. For example, thermal actuation (heating) can reverse deformation(s) by inducing a change in state (e.g., phase change) in the actuator material, inducing a temporary elevated internal stress that promotes a shape change toward the preferred geometric configuration. For a shape memory alloy, the change in state can be from a martensitic phase (alternatively, R-phase) to an austenitic phase. For a shape memory polymer, the change in state can be via a glass transition temperature or a melting temperature. The change in state can reverse deformation(s) of the material—for example, deformation with respect to its preferred geometric configuration—without any (e.g., externally) applied stress to the actuation element. That is, a deformation that is present in the material at a first temperature (e.g., body temperature)

can be (e.g., thermally) recovered and/or altered by raising the material to a second (e.g., higher) temperature. Upon cooling (and changing state, e.g., back to martensitic phase), the actuation element retains its preferred geometric configuration. With the material in this relatively cooler-temperature condition it may require a lower force or stress to thermoelastically deform the material, and any subsequently applied external stress can cause the actuation element to once again deform away from the original geometric configuration.

The actuation element(s) can be processed such that a transition temperature at which the change in state occurs (e.g., the austenite start temperature, the austenite final temperature, etc.) is above a threshold temperature (e.g., body temperature). For example, the transition temperature can be set to be about 45 deg. C., about 50 deg. C., about 55 deg. C., or about 60 deg. C. In some embodiments, the actuator material is heated from body temperature to a temperature above the austenite start temperature (or alternatively above the R-phase start temperature) such that an upper plateau stress (e.g., "UPS_body temperature") of the material in a first state (e.g., thermoelastic martensitic phase, or thermoelastic R-phase at body temperature) is lower than an upper plateau stress (e.g., "UPS_actuated temperature") of the material in a heated state (e.g., superelastic state), which achieves partial or full free recovery. For example, the actuator material can be heated such that UPS_actuated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase at body temperature") is lower than a lower plateau stress (e.g., "LPS") of the material in a heated state (e.g., superelastic state), which achieves partial or full free recovery. For example, the actuator material can be aged such that LPS activated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase) is higher than a lower plateau stress of the material in a heated state, which achieves partial free recovery. For example, the actuator material can be aged such that LPS activated temperature<UPS_body temperature.

The flow control assembly can be formed such that the actuation elements have substantially the same preferred geometric configuration (e.g., memory shape, or length, L0). The flow control assembly can be assembled such that, upon introduction into a patient (e.g., implantation), at least one (e.g., a first) actuation element/shape memory element has been deformed with respect to its preferred geometric configuration (e.g., to have L1≠L0), while at least one other opposing (e.g., a second) actuation element/shape memory element positioned adjacent to the first actuation element is substantially at its preferred geometric configuration (e.g., L0). In other embodiments, however, both the first and second actuation elements may be deformed with respect to their corresponding preferred geometric configuration upon introduction into the patient (e.g., the first actuation element is contracted relative to its preferred geometric configuration and the second actuation element is expanded relative to its preferred geometric configuration).

In some embodiments of the present technology, L1>L0—for example, the deformed first actuation element is elongated with respect to its preferred "shape memory" length. In some embodiments, L1<L0—for example, the deformed first actuation element is compressed with respect to its preferred shape memory length. The flow control assembly can be formed such that, in operation, its overall dimension (e.g., overall length) is substantially fixed (e.g., L0+L1=a constant). For example, (e.g., outermost) ends of the actuation elements can be fixed, such that movement of the actuation elements occurs between the points of fixation. The overall geometry of the actuation elements, along with the lengths, can be selected such that, in operation, deformation within the actuation elements remains below about 10%, about 9%, about 8%, about 7%, or about 6%.

The (e.g., first and second) actuation elements are arranged such that a movement (e.g., deflection or deformation) of the first actuation element/first shape memory element is accompanied by (e.g., causes) an opposing movement of the second actuation element/second shape memory element. The movement can be a deflection or a deformation. In operation, selective heating of the first actuation element of the flow control assembly causes it to move to and/or toward its preferred geometric configuration (e.g., revert from L1 to L0), moving the coupled moveable element. At the same time, the elongation of the first actuation element is accompanied by (e.g., causes) a compression of the second actuation element (e.g., from L0 to L1). The second actuation element is not heated (e.g., remains at body temperature), and therefore the second actuation element deforms (e.g., remains martensitic and compresses). The first actuation element cools following heating, and returns to a state in which it can be plastically deformed. To reverse the configuration of the flow control assembly (e.g., the position of the moveable element), the second actuation element is heated to move to and/or toward its preferred geometric configuration (e.g., from L1 to L0). The return of the second actuation element to its preferred geometric configuration causes the moveable element to move back to its prior position, and compresses the first actuation element (e.g., from L0 to L1). The position of the moveable element for the flow control assembly can be repeatably toggled (e.g., between open and closed) by repeating the foregoing operations. The heating of an actuation element can be accomplished via application of incident energy (e.g., via a laser or inductive coupling). Further, as mentioned above, the source of the incident energy may be external to the patient (e.g., non-invasive).

FIGS. 10A-10D illustrate an embodiment of a flow control assembly 1000 configured in accordance with select embodiments of the present technology. The flow control assembly 1000 is configured for use with a system or device for shunting, draining, or otherwise moving fluid from a first body region or chamber to a second body region or chamber. Although the flow control assembly 100 is shown schematically, one skilled in the art will appreciate that the principles and modes of operation discussed with respect to the flow control assembly 100 can apply to any of the flow control assemblies disclosed herein. Accordingly, the flow control assembly 100 can be generally similar to and/or the same as the flow control assemblies described previously.

Referring collectively to FIGS. 10A-10D, the flow control assembly 1000 can include a first actuation element 1001 and a second actuation element 1002. The first actuation element 1001 can extend between a control element 1003 and a first anchoring element 1004. The second actuation element 1002 can extend between the control element 1003 and a second anchoring element 1004. The first anchoring element 1004 and the second anchoring element 1005 can be secured to a generally static component of the system or device for shunting fluid (not shown). In other embodiments, the first anchoring element 1004 and/or the second anchoring element 1005 can be omitted and the first actuation element 1001 and/or the second actuation element 1002 can be secured directly to a portion of the device or system for shunting fluid (not shown). As provided above, the control element 1003 can be formed to interface with (e.g., at least partially block) a corresponding port on the system or device (not shown). In other embodiments, the control element 1003 can be an intermediate element to drive a flow control element (not shown) that interfaces with or otherwise engages a lumen or orifice of the device or system for shunting fluid (not shown).

The first actuation element 1001 and the second actuation element 1002 can be composed of a shape memory material, such as a shape memory alloy (e.g., nitinol). Accordingly, the first actuation element 1001 and the second actuation element 1002 can be transitionable between at least a first material phase or state (e.g., a martensitic material state, an R-phase material state, etc.) and a second material phase or state (e.g., an austenitic material state, an R-phase material state, etc.). In the first state, the first actuation element 1001 and the second actuation element 1002 may be deformable (e.g., plastic, malleable, compressible, expandable, etc.). In the second state, the first actuation element 1001 and the second actuation element 1002 may have a preference toward a specific preferred geometry (e.g., original geometry, manufactured geometry, heat set geometry, etc.). The first actuation element 1001 and the second actuation element 1002 can be transitioned between the first state and the second state by applying energy (e.g., heat) to the actuation elements to heat the actuation elements above a transition temperature. In some embodiments, the transition temperature for both the first actuation element 1001 and the second actuation element 1002 is above an average body temperature (e.g., an average body temperature in the eye). Accordingly, both the first actuation element 1001 and the second actuation element 1002 are typically in the deformable first state when the flow control assembly 1000 is implanted in the body until they are heated (e.g., actuated).

If an actuation element (e.g., the first actuation element 1001) is deformed relative to its preferred geometry while in the first state, heating the actuation element (e.g., the first actuation element 1001) above its transition temperature causes the actuation element to transition to the second state and therefore transition from the deformed shape to and/or toward its preferred geometry. Heat can be applied to the actuation elements via an energy source positioned external to the body (e.g., a laser), RF heating, resistive heating, or the like. In some embodiments, the first actuation element 1001 can be selectively heated independently of the second actuation element 1002, and the second actuation element 1002 can be selectively heated independently of the first actuation element 1001.

Figure 10A:
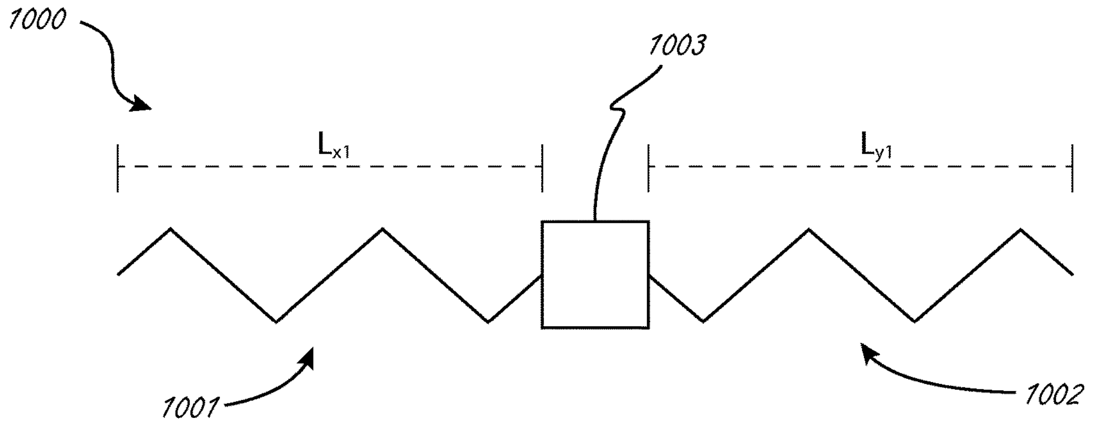
FIGS. 10A-10D illustrate an actuation assembly configured in accordance with embodiments of the present technology.

Referring to FIG. 10A, the first actuation element 1001 and the second actuation element 1002 are shown in a state before being secured to the first and second anchoring elements. In particular, the first actuation element 1001 and the second actuation 1002 are in their unbiased preferred geometries. In the illustrated embodiment, the first actuation element 1001 has an original shape having a length Lx1, and the second actuation element 1002 has an original shape having a length Ly1. In some embodiments, Lx1 is equal to Ly1. In other embodiments, Lx1 is less than or greater than (i.e., not equal to) Ly1.

Figure 10B:
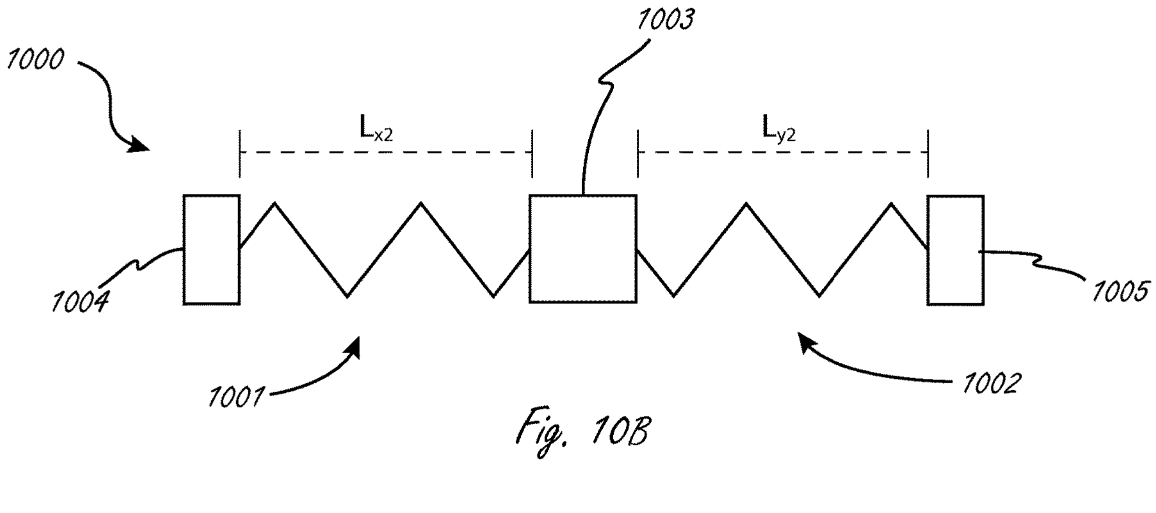

FIG. 10B illustrates the flow control assembly 1000 in a first (e.g., composite) configuration after the first actuation element 1001 has been secured to the first anchoring element 1004, and the second actuation element 1002 has been secured to the second anchoring element 1005. In the first configuration, both the first actuation element 1001 and the second actuation element 1002 are at least partially deformed relative to their preferred geometries. For example, the first actuation element 1001 is compressed (e.g., shortened) relative to its preferred geometry (FIG. 10A) such that it assumes a second length Lx2 that is less than the first length Lx1. Likewise, the second actuation element 1002 is also compressed (e.g., shortened) relative to its preferred geometry (FIG. 10A) such that it assumes a second length Ly2 that is less than the first length Ly1. In the illustrated embodiment, Lx1 is equal to Ly1, although in other embodiments Lx1 can be less than or greater than (i.e., not equal to) Ly1. In other embodiments, the first actuation element 1001 and/or the second actuation element 1002 are stretched (e.g., lengthened) relative to their preferred geometries before being secured to the anchoring elements. For example, in some embodiments both the first actuation element 1001 and the second actuation element 1002 are stretched relative to their preferred geometries. In other embodiments, the first actuation element 1001 is compressed (e.g., shortened) relative to its preferred geometry and the second actuation element 1002 is stretched (e.g., lengthened) relative to its preferred geometry. In some embodiments, only one of the actuation elements (e.g., the first actuation element 1001) is deformed relative to its preferred geometry, and the other actuation element (e.g., the second actuation element 1002) retains its preferred geometry.

Figure 10C:
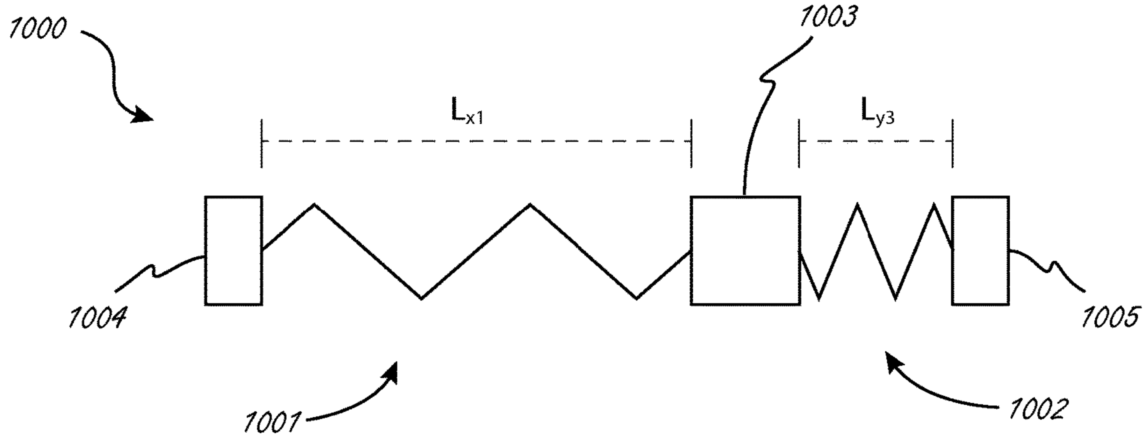

FIG. 10C illustrates the flow control assembly 1000 in a second configuration different than the first configuration. In particular, in the second configuration, the flow control assembly 1000 has been actuated relative to the first configuration shown in FIG. 10B to transition the first actuation element 1001 from the first (e.g., martensitic) state to the second (e.g., austenitic) state. Because the first actuation element 1001 was deformed (e.g., compressed) relative to its preferred geometry while in the first configuration, heating the first actuation element 1001 above its transition temperature causes the first actuation element 1001 to move to and/or toward its preferred geometry having a length Lx1 (FIG. 10A). As described above, the first anchoring element 1004 and the second anchoring element 1005 are fixedly secured to a generally static structure (e.g., such that a distance between the first anchoring element 1004 and the second anchoring element 1005 does not change during actuation of the first actuation element 1001). Accordingly, as the first actuation element 1001 increases in length toward its preferred geometry, the second actuation element 1002, which is unheated and therefore remains in the generally deformable (e.g., martensitic) state, is further compressed to a length Ly3 that is less than Ly1 and Ly2. In the illustrated embodiment, this moves the control element away from the first anchoring element 1004 and towards the second anchoring element 1005.

Figure 10D:
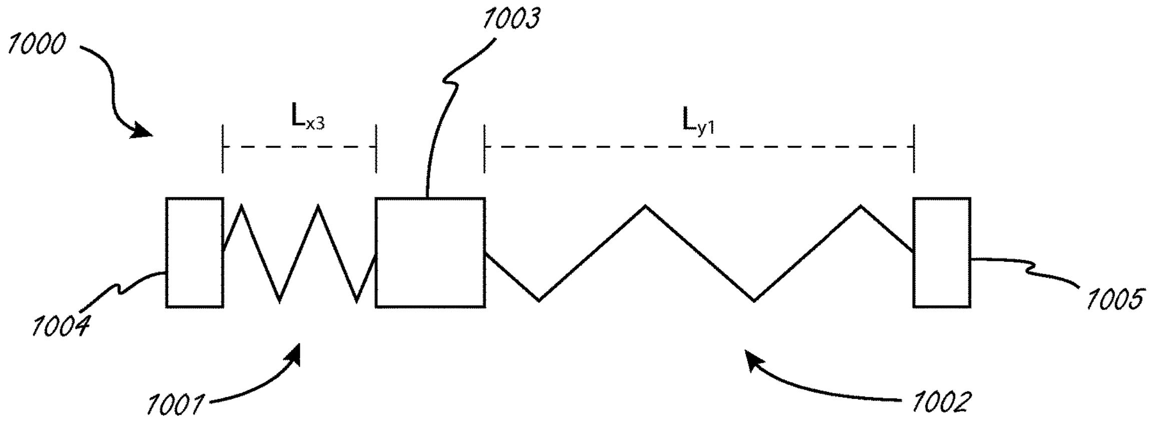

FIG. 10D illustrates the flow control assembly 1000 in a third configuration different than the first configuration and the second configuration. In particular, in the third configuration the flow control assembly 1000 has been actuated relative to the second configuration shown in FIG. 10C to transition the second actuation element 1002 from the first (e.g., martensitic) state to the second (e.g., austenitic) state. Because the second actuation element 1002 was deformed (e.g., compressed) relative to its preferred geometry while in the second configuration, heating the second actuation element 1002 above its transition temperature causes the second actuation element 1002 to and/or toward its preferred geometry having a length Ly1 (FIG. 10A). As described above, the first anchoring element 1004 and the second anchoring element 1005 are fixedly secured to a generally static structure (e.g., such that the distance between the first anchoring element 1004 and the second anchoring element 1005 does not change during actuation of the second actuation element 1002). Accordingly, as the second actuation element 1002 increases in length toward its preferred geometry, the first actuation element 1001, which is unheated and therefore remains in the generally deformable (e.g., martensitic) state, is further deformed (e.g., compressed) relative to its preferred geometry to a length Lx3 that is less than Lx1 and Lx2. In the illustrated embodiment, this moves the control element 1003 away from the second anchoring element 1005 and towards the first anchoring element 1004 (e.g., generally opposite the direction the control element 1003 moves when the first actuation element 1001 is actuated).

The flow control assembly 1000 can be repeatedly transitioned between the second configuration and the third configuration. For example, the flow control assembly 1000 can be returned to the second configuration from the third configuration by heating the first actuation element 1001 above its transition temperature once the second actuation element 1002 has returned to the deformable first state (e.g., by allowing the second actuation element 1002 to cool below the transition temperature). Heating the first actuation element 1001 above its transition temperature causes the first actuation element 1001 to move to and/or toward its preferred geometry, which in turn pushes the control element 1003 back towards the second anchoring element 1005 and transitions the flow control assembly 1000 to the second configuration (FIG. 10C). Accordingly, the flow control assembly 1000 can be selectively transitioned between a variety of configurations by selectively actuating either the first actuation element 1001 or the second actuation element 1002. After actuation, the flow control assembly 1000 can be configured to substantially retain the given configuration until further actuation of the opposing actuation element. In some embodiments, the flow control assembly 1000 can be transitioned to intermediate configurations between the second configuration and the third configuration (e.g., the first configuration) by heating a portion of the first actuation element 1001 or the second actuation element 1002.

As provided above, heat can be applied to the actuation elements via an energy source positioned external to the body (e.g., a laser), RF heating, resistive heating, or the like. In some embodiments, the first actuation element 1001 can be selectively heated independently of the second actuation element 1002, and the second actuation element 1002 can be selectively heated independently of the first actuation element 1001. For example, in some embodiments, the first actuation element 1001 is on a first electrical circuit and/or responds to a first frequency range for selectively and resistively heating the first actuation element 1001 and the second actuation element 1002 is on a second electrical circuit and/or responds to a second frequency range for selectively and resistively heating the second actuation element 1002. As described in detail above, selectively heating the first actuation element 1001 moves the control element 1003 in a first direction and selectively heating the second actuation element 1002 moves the control element 1003 in a second direction generally opposite the first direction.

D. Examples

Several aspects of the present technology are set forth in the following examples.

1. A variable flow shunt for treatment of glaucoma in a human patient, the variable flow shunt comprising:
   - a drainage element having a first opening, a second opening, and a lumen extending therethrough, wherein, when implanted in an eye, the drainage element is configured to fluidly connect an anterior chamber and a target outflow location;
   - a flow control assembly operably coupled to the drainage element and configured to at least partially control the flow of fluid through at least one of the first opening or the second opening; and
   - an outer membrane encasing the flow control assembly and at least one of the first opening or the second opening, wherein the outer membrane includes a plurality of apertures fluidly coupling an interior of the outer membrane with an environment exterior to the outer membrane.

2. The variable flow shunt of example 1 wherein the outer membrane includes a bladder portion encasing the flow control assembly and an elongated portion at least partially encasing the drainage element.

3. The variable flow shunt of example 2 wherein the bladder portion includes a proximal portion adjacent the elongated portion and a distal portion spaced apart from the elongated portion, and wherein the distal portion includes the plurality of apertures and the proximal portion does not include any of the plurality of apertures.

4. The variable flow shunt of example 2 wherein the bladder portion is generally dome shaped.

5. The variable flow shunt of example 2 wherein the bladder portion includes a generally curved surface and a generally flat surface.

6. The variable flow shunt of example 5 wherein the generally flat surface is textured.

7. The variable flow shunt of example 2 wherein the bladder portion has a height and a width, and wherein the width is greater than the height.

8. The variable flow shunt of any of examples 2 wherein the tubular portion includes a ring configured to reduce and/or prevent axial translation of the shunt when the shunt is implanted in the patient.

10. The variable flow shunt of example 8 wherein the ring is positionable in a region exterior to the anterior chamber.

11. The variable flow shunt of example 1 wherein the outer membrane includes one or more attachment features for securing the shunt to native tissue.

12. The variable flow shunt of example 11 wherein the one or more attachment features include one or more suture holes.

13. The variable flow shunt of example 1 wherein the outer membrane is configured to at least partially reduce a backflow pressure through the drainage element.

14. The variable flow shunt of example 1 wherein the drainage element includes a flow tube.

15. A variable flow shunt for treatment of glaucoma in a human patient, the variable flow shunt comprising:
   - a drainage element having a first opening, a second opening, and a lumen extending between the first opening and the second opening, wherein, when implanted in an eye, the drainage element is configured to fluidly connect an anterior chamber and a target outflow location;

a flow control assembly coupled to the drainage element and configured to at least partially control the flow of fluid through at least one of the first opening or the second opening; and an outer membrane encasing the flow control assembly and at least one of the first opening or the second opening, wherein the outer membrane includes a plurality of apertures for draining fluid contained within the outer membrane, and wherein the outer membrane is configured to reduce a backflow pressure through the drainage element.

16. The variable flow shunt of example 15 wherein the outer membrane includes a bladder portion encasing the flow control assembly and an elongated portion at least partially encasing the drainage element.

17. The variable flow shunt of example 16 wherein the bladder portion includes a proximal portion adjacent the elongated portion and a distal portion spaced apart from the elongated portion, and wherein the distal portion includes the plurality of apertures and the proximal portion does not include any of the plurality of apertures.

18. A system for treating glaucoma in a human patient, the system comprising:

a shunt configured to fluidly connect an anterior chamber of an eye and a target drainage location, the shunt having an inflow portion positionable within the anterior chamber and an outflow portion positionable within the target drainage location; and a bladder encasing the outflow portion of the shunt, wherein the bladder is configured to reduce a backflow pressure through the shunt to facilitate the drainage of aqueous through the shunt.

19. The system of example 18 wherein the bladder includes a plurality of apertures fluidly coupling an interior of the bladder with an environment external to the bladder.

20. The system of example 18, further comprising a flow control assembly coupled to the shunt and configured to control the flow of fluid through at least one of the inflow portion or the outflow portion.

21. The system of example 20, wherein the flow control assembly is positioned within the bladder and is configured to control the flow of fluid through the outflow portion.

22. The system of example 20 wherein the bladder includes one or more attachment features for securing the shunt to native tissue.

23. The system of example 22 wherein the one or more attachment features include one or more suture holes.

24. The system of example 18 wherein the bladder is generally dome-shaped.

25. The system of example 18 wherein the bladder includes a generally curved surface and a generally flat surface.

26. The system of example 25 wherein the generally flat surface is textured.

27. The system of example 18 wherein the bladder has a height and a width, and wherein the width is greater than the height.

28. A system for treating glaucoma in a human patient, the system comprising:

a shunt configured to fluidly connect an anterior chamber of an eye and a target drainage location, the shunt having an inflow portion positionable within the anterior chamber and an outflow portion positionable within the target drainage location;

a flow control assembly coupled to the shunt and configured to control the flow of fluid through the inflow portion of the shunt; and a bladder encasing the flow control assembly and the inflow portion of the shunt, wherein the bladder includes a plurality of openings that, when the system is implanted in the eye, permits aqueous to flow from an environment external to the bladder and into an interior of the bladder.

29. The system of example 28 wherein the flow control assembly includes one or more shape memory actuation elements configured to control the flow of fluid through the inflow portion of the shunt.

30. A variable flow shunt for treatment of glaucoma in a human patient, the variable flow shunt comprising:

an elongated flow tube having a lumen extending therethrough between (a) an inflow portion configured for placement within an anterior chamber in a region outside of an optical field of view of an eye of the patient, and (b) an outflow portion at a different location of the eye, wherein the outflow portion has an aperture in fluid communication with the lumen;

a flow control assembly positioned along the flow tube adjacent the distal flow portion, wherein the flow control assembly includes a control element moveable through a plurality of positions in response to energy; and an outer membrane encasing the flow control assembly and configured to at least partially anchor the variable flow shunt in a target position when the variable flow shunt is implanted in the eye, wherein the outer membrane includes a plurality of perforations configured such that fluid flowing out of the outflow tube via the aperture flows out of the outer membrane via the plurality of perforations.

31. The variable flow shunt of example 30 wherein the control element is moveable from a first position at least partially blocking the aperture to a second position (a) not blocking the aperture and/or (b) blocking less of the aperture than the first position.

32. The variable flow shunt of example 30 or 31 wherein the control element is moveable from a first position that provides a first level of fluid flow reduction through the aperture and a plurality of second positions that provide increasing levels of fluid flow through the aperture.

33. The variable flow shunt of any one of examples 30-32 wherein the control element is moveable between a first position that provides a first level of fluid flow reduction through the aperture and a plurality of second positions that provide increasing levels of fluid flow reduction through the aperture.

34. The variable flow shunt of any one of examples 30-33 wherein the flow control assembly includes a spring element coupled to the control element, wherein the spring element is configured to move the control element through at least a subset of the plurality of positions.

35. The variable flow shunt of example 34 wherein the spring element is configured to transform from a first shape to a second shape upon application of energy to the spring element.

36. The variable flow shunt of example 34 or example 35 wherein the spring element moves the control element from a first position to a second position upon application of energy to the spring element.

37. The variable flow shunt of example 30 wherein the flow control assembly includes:

a first spring element coupled to a first anchor at a first end and the flow control element at a second end, wherein applying energy to the first spring element causes the flow control element to slidably move along the flow tube in a first direction; and a second spring element coupled to a second anchor at a first end and the flow control element at a second end, wherein applying energy to the second spring element causes the flow control element to slidably move along the flow tube in a second direction.

38. The variable flow shunt of example 37 wherein the first direction is away from the first anchor and the second direction is away from the second anchor.

39. The variable flow shunt of any one of examples 35-38 wherein the spring element is composed of a shape memory material.

40. The variable flow shunt of any one of examples 35-39 wherein the spring element is nitinol.

41. The variable flow shunt of any of examples 35-40 wherein the energy is light or heat.

42. The variable flow shunt of any one of examples 30-41 wherein the flow control assembly is formed from a flat nitinol sheet.

43. The variable flow shunt of any one of examples 30-42 wherein the outer membrane extends along a length of the flow tube and has a generally circular cross-sectional shape.

44. The variable flow shunt of any one of examples 30-43 wherein the outer membrane has a generally dome-shaped cross-sectional shape.

45. The variable flow shunt of any one of examples 30-44 wherein the elongated flow tube comprises:

an inflow tube including the inflow portion configured for placement within the anterior chamber, wherein the inflow tube is composed of a first material having a first rigidity; and an outflow tube coupled to the inflow tube and including the outflow portion, wherein the outflow tube is composed of a second material having a second rigidity greater than the first rigidity.

46. An adjustable flow shunt for treating glaucoma in a human patient, the shunt comprising:

an elongated drainage tube having an inflow region and an outflow region, wherein the outflow region includes one or more apertures that permit fluid to exit the elongated drainage tube;

a flow control assembly coupled to the elongated drainage tube at the outflow region, wherein the flow control assembly is configured to control fluid flow through the one or more apertures; and a protective membrane at least partially surrounding the flow control assembly, wherein the protective membrane includes one or more perforations that permit fluid within the protective membrane to flow out of the protective membrane.

47. The adjustable flow shunt of example 46 wherein the protective membrane includes a bladder portion surrounding the flow control assembly and a tubular portion surrounding at least a portion of the elongated drainage tube.

48. The adjustable flow shunt of example 46 or example 47 wherein the protective membrane has a circular or oval cross-sectional shape.

49. The adjustable flow shunt of example 46 or example 47 wherein the protective membrane has a generally dome-shaped cross-sectional shape.

50. The adjustable flow shunt of any one of examples 46-49 wherein the elongated drainage tube has an oval cross-sectional shape.

51. The adjustable flow shunt of any one of examples 46-50 wherein the protective membrane has a height and a width, and wherein the width is greater than the height.

52. The adjustable flow shunt of any one of examples 46-51 wherein the protective membrane is substantially flat.

53. The adjustable flow shunt of any one of examples 46-52 wherein the protective membrane is configured to at least partially anchor the adjustable flow shunt in a target position when the adjustable flow shunt is implanted in an eye.

54. A method of treating glaucoma, the method comprising:

implanting a shunt into an eye wherein, when implanted, the shunt receives fluid from an anterior chamber of the eye;

after allowing tissue surrounding the shunt to at least partially heal, non-invasively adjusting a flow of fluid through the shunt.

55. The method of example 54 wherein non-invasively adjusting the flow of fluid through the shunt comprises applying energy to the shunt.

56. The method of example 55 wherein the energy is light or heat.

57. The method of example 54 wherein the shunt comprises a flow control element composed at least partially of shape-memory material, and wherein non-invasively adjusting a flow of fluid through the shunt comprises transforming the flow control element from a first position to a second position.

58. A method of treating a patient having glaucoma, the method comprising:

implanting an adjustable flow shunt having a flow control mechanism into the patient's eye, wherein, following implantation, the adjustable flow shunt fluidly connects an anterior chamber of the eye and a suitable drainage site; and selectively adjusting the flow control mechanism to alter the drainage of aqueous through the adjustable flow shunt.

59. The method of example 58 wherein selectively adjusting the flow control mechanism comprises non-invasively adjusting the flow control mechanism.

60. The method of example 58 or example 59 wherein selectively adjusting the flow control mechanism comprises applying energy to at least a portion of the flow control mechanism from a source external to the patient.

61. The method of example 60 wherein applying energy causes the flow control mechanism to transition from a first position to a second position.

62. The method of example 61 wherein the first position enables a first rate of fluid flow through the shunt and the second position enables a second rate of fluid flow greater than the first rate through the shunt.

63. The method of example 61 wherein the first position enables a first rate of fluid flow through the shunt and the second position enables a second rate of fluid flow less than the first rate through the shunt.

64. The method of any one of examples 60-63 wherein the energy is heat or light.

65. A method of treating a patient having glaucoma, the method comprising:

implanting an adjustable flow shunt into the patient's eye, wherein the adjustable flow shunt includes a tubular element and a flow control mechanism, and wherein, following implantation, the adjustable flow shunt receives fluid from an anterior chamber of the eye; and non-invasively adjusting a flow of fluid through the shunt by axially translating at least a portion of the flow control mechanism with respect to the tubular element.

66. The method of example 65 wherein axially translating at least a portion of the flow control mechanism comprises applying energy to the shunt.

67. The method of example 66 wherein the energy is light or heat.

68. The method of any one of examples 65-67 wherein the tubular element includes an outflow aperture, and wherein axially translating at least a portion of the flow control mechanism changes the flow of fluid through the outflow aperture.

69. A method of manufacturing an adjustable flow shunt having a shunt and a flow control assembly, the method comprising:

forming a flow control assembly from a sheet of nitinol, the flow control assembly having a flow control element and a spring element; and attaching the formed flow control assembly to the shunt such that the flow control assembly is configured to at least partially control the flow of fluid through the shunt.

70. The method of example 69 wherein forming the flow control assembly comprises laser cutting the flow control assembly from the sheet of nitinol.

71. The method of example 69 or example 70, further comprising biasing the spring element before attaching the formed flow control assembly to the shunt.

72. A variable flow shunt, comprising:

a drainage element having a first opening, a second opening, and a lumen extending therethrough, wherein, when implanted in a patient, the drainage element is configured to fluidly connect a first body region and a second body region;

a flow control assembly operably coupled to the drainage element and configured to at least partially control the flow of fluid through at least one of the first opening or the second opening; and an outer membrane encasing the flow control assembly and at least one of the first opening or the second opening, wherein the outer membrane includes a plurality of apertures fluidly coupling an interior of the outer membrane with an environment exterior to the outer membrane.

73. The variable flow shunt of example 1 wherein the outer membrane includes a bladder portion encasing the flow control assembly and an elongated portion at least partially encasing the drainage element.

74. The variable flow shunt of example 73 wherein the bladder portion includes a proximal portion adjacent the elongated portion and a distal portion spaced apart from the elongated portion, and wherein the distal portion includes the plurality of apertures and the proximal portion does not include any of the plurality of apertures.

75. The variable flow shunt of example 73 or 74 wherein the bladder portion is generally dome shaped.

76. The variable flow shunt of any of examples 73-75 wherein the bladder portion includes a generally curved surface and a generally flat surface.

77. The variable flow shunt of example 76 wherein the generally flat surface is textured.

78. The variable flow shunt of any of examples 73-77 wherein the bladder portion has a height and a width, and wherein the width is greater than the height.

79. The variable flow shunt of any of examples 72-77 wherein the tubular portion includes a ring configured to reduce and/or prevent axial translation of the shunt when the shunt is implanted in the patient.

80. The variable flow shunt of example 79 wherein the ring is positionable in a region exterior to the anterior chamber.

81. The variable flow shunt of any of examples 72-80 wherein the outer membrane includes one or more attachment features for securing the shunt to native tissue.

82. The variable flow shunt of example 81 wherein the one or more attachment features include one or more suture holes.

83. The variable flow shunt of any of examples 72-82 wherein the outer membrane is configured to at least partially reduce a backflow pressure through the drainage element.

84. The variable flow shunt of any of examples 72-83 wherein the drainage element includes a flow tube.

85. A variable flow shunt, comprising:

a drainage element having a first opening, a second opening, and a lumen extending between the first opening and the second opening, wherein, when implanted in a patient, the drainage element is configured to fluidly connect a first body region and a second body region;

a flow control assembly coupled to the drainage element and configured to at least partially control the flow of fluid through at least one of the first opening or the second opening; and an outer membrane encasing the flow control assembly and at least one of the first opening or the second opening, wherein the outer membrane includes a plurality of apertures for draining fluid contained within the outer membrane, and wherein the outer membrane is configured to reduce a backflow pressure through the drainage element.

86. The variable flow shunt of example 85 wherein the outer membrane includes a bladder portion encasing the flow control assembly and an elongated portion at least partially encasing the drainage element.

87. The variable flow shunt of example 86 wherein the bladder portion includes a proximal portion adjacent the elongated portion and a distal portion spaced apart from the elongated portion, and wherein the distal portion includes the plurality of apertures and the proximal portion does not include any of the plurality of apertures.

88. A system for treating a medical condition in a patient, the system comprising:

a shunt configured to fluidly connect a first body region and a second body region of the patient, the shunt having an inflow portion positionable within the first body region and an outflow portion positionable within the second body location; and a bladder encasing the outflow portion of the shunt, wherein the bladder is configured to reduce a backflow pressure through the shunt to facilitate the drainage of fluid from the first body region, through the shunt, and into the second body region.

89. The system of example 88 wherein the bladder includes a plurality of apertures fluidly coupling an interior of the bladder with an environment external to the bladder.

90. The system of example 88 or 89, further comprising a flow control assembly coupled to the shunt and configured to control the flow of fluid through at least one of the inflow portion or the outflow portion.

91. The system of example 90, wherein the flow control assembly is positioned within the bladder and is configured to control the flow of fluid through the outflow portion.

92. The system of any of examples 88-91 wherein the bladder includes one or more attachment features for securing the shunt to native tissue.

93. The system of example 92 wherein the one or more attachment features include one or more suture holes.

94. The system of any of examples 88-93 wherein the bladder is generally dome-shaped.

95. The system of any of examples 88-94 wherein the bladder includes a generally curved surface and a generally flat surface.

96. The system of example 95 wherein the generally flat surface is textured.

97. The system of any of examples 88-96 wherein the bladder has a height and a width, and wherein the width is greater than the height.

98. The system of any of examples 88-97 wherein the shunt is configured to be implanted in the patient's eye, and wherein the first body region is an anterior chamber and the second body region is a target outflow location within the patient's eye.

99. A system for treating a medical condition in a patient, the system comprising:

- a shunt configured to fluidly connect a first body region and a second body region of the patient, the shunt having an inflow portion positionable within the first body region and an outflow portion positionable within the second body region;
- a flow control assembly coupled to the shunt and configured to control the flow of fluid through the inflow portion of the shunt; and
- a bladder encasing the flow control assembly and the inflow portion of the shunt, wherein the bladder includes a plurality of openings that, when the system is implanted in the eye, permits fluid to flow from an environment external to the bladder in the first body region and into an interior of the bladder.

100. The system of example 99 wherein the flow control assembly includes one or more shape memory actuation elements configured to control the flow of fluid through the inflow portion of the shunt.

101. The system of example 100 wherein the shunt is configured to be implanted in the patient's eye, and wherein the first body region is an anterior chamber and the second body region is a target outflow location within the patient's eye.

102. An implantable medical device, comprising:

- an actuation assembly configured to control one or more operations of the implantable medical device, wherein the actuation assembly includes at least one shape memory actuation element having a preferred geometry, and wherein, when the at least one shape memory actuation element is deformed relative to its preferred geometry, heating the shape memory actuation element above a transition temperature causes the actuation element to move toward its preferred geometry and adjust an operation of the implantable medical device; and
- a bladder encasing the actuation assembly, wherein the bladder is configured to permit energy from an external energy source to penetrate the bladder and heat the actuation element.

103. The device of example 102 wherein the bladder includes a plurality of apertures.

104. The device of example 102 or 103 wherein the bladder includes one or more attachment features for anchoring at least a portion of the implantable medical device when the device is implanted in a patient.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the adjustable flow shunts described herein may be combined with any of the features of the other adjustable flow shunts described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with adjustable flow shunts have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A variable flow shunt, comprising:

- a drainage element having a first opening, a second opening, and a lumen extending therethrough, wherein, when implanted in a patient, the drainage element is configured to fluidly connect a first body region and a second body region;
- a flow control assembly operably coupled to the drainage element and configured to at least partially control the flow of fluid through at least one of the first opening or the second opening, wherein at least a portion of the flow control assembly is activatable via light and/or heat; and
- an outer membrane encasing at least the portion of the flow control assembly that is activatable via light and/or heat and at least one of the first opening or the second opening, wherein the outer membrane includes a plurality of apertures fluidly coupling an interior of the outer membrane with an environment exterior to the outer membrane.

2. The variable flow shunt of claim 1, wherein the outer membrane includes a bladder portion encasing the portion of the flow control assembly and an elongated portion at least partially encasing the drainage element.

3. The variable flow shunt of claim 2, wherein the bladder portion includes a proximal portion adjacent the elongated portion and a distal portion spaced apart from the elongated portion, and wherein the distal portion includes the plurality of apertures and the proximal portion does not include any of the plurality of apertures.

4. The variable flow shunt of claim 2, wherein the bladder portion is generally dome shaped.

5. The variable flow shunt of claim 2, wherein the bladder portion includes a generally curved surface and a generally flat surface.

6. The variable flow shunt of claim 5, wherein the generally flat surface is textured.

7. The variable flow shunt of claim 2, wherein the bladder portion has a height and a width, and wherein the width is greater than the height.

8. The variable flow shunt of claim 2, wherein the elongated portion includes a ring configured to reduce and/or prevent axial translation of the shunt when the shunt is implanted in the patient.

9. The variable flow shunt of claim 8, wherein the ring is positionable in a region exterior to the first body region.

10. The variable flow shunt of claim 1, wherein the outer membrane includes one or more attachment features for securing the shunt to native tissue.

11. The variable flow shunt of claim 10, wherein the one or more attachment features include one or more suture holes.

12. The variable flow shunt of claim 1, wherein the outer membrane is configured to at least partially reduce a back-flow pressure through the drainage element.

13. The variable flow shunt of claim 1, wherein the drainage element includes a flow tube.

14. The variable flow shunt of claim 1, wherein the flow control assembly includes a first actuation element and a second actuation element, wherein the first actuation element and the second actuation element are both composed of shape memory material, and wherein the first actuation element and the second actuation element act in opposition and can be selectively and independently actuated.

15. The variable flow shunt of claim 1, wherein the flow control assembly is disposed on an outer surface of the drainage element.

16. The variable flow shunt of claim 1, wherein the outer membrane is configured to have a spherical, ellipsoidal, or conical shape.

17. The variable flow shunt of claim 1, wherein at least the portion of the flow control assembly is activatable via light from a laser.

18. A variable flow shunt, comprising:

a drainage element having a first opening, a second opening, and a lumen extending between the first opening and the second opening, wherein, when implanted in a patient, the drainage element is configured to fluidly connect a first body region and a second body region;

a flow control assembly coupled to the drainage element and configured to at least partially control the flow of fluid through at least one of the first opening or the second opening, wherein at least a portion of the flow control assembly is activatable via light and/or heat; and an outer membrane encasing at least the portion of the flow control assembly that is activatable via light and/or heat and at least one of the first opening or the second opening, wherein the outer membrane includes a plurality of apertures for draining fluid contained within the outer membrane, and wherein the outer membrane is configured to reduce a backflow pressure through the drainage element.

19. The variable flow shunt of claim 18, wherein the outer membrane includes a bladder portion encasing the portion of the flow control assembly and an elongated portion at least partially encasing the drainage element.

20. The variable flow shunt of claim 19, wherein the bladder portion includes a proximal portion adjacent the elongated portion and a distal portion spaced apart from the elongated portion, and wherein the distal portion includes the plurality of apertures and the proximal portion does not include any of the plurality of apertures.

21. A system for treating a medical condition in a patient, the system comprising:

a shunt configured to fluidly connect a first body region and a second body region of the patient, the shunt having an inflow portion positionable within the first body region and an outflow portion positionable within the second body region;

a flow control assembly coupled to the shunt and configured to control the flow of fluid through the inflow portion of the shunt, wherein at least a portion of the flow control assembly is activatable via light and/or heat; and a bladder encasing at least the portion of the flow control assembly that is activatable via light and/or heat and the inflow portion of the shunt, wherein the bladder includes a plurality of openings that, when the system is implanted in the eye, permits fluid to flow from an environment external to the bladder in the first body region and into an interior of the bladder.

22. The system of claim 21, wherein the flow control assembly includes one or more shape memory actuation elements configured to control the flow of fluid through the inflow portion of the shunt.

23. The system of claim 21, wherein the shunt is configured to be implanted in an eye of the patient, and wherein the first body region is an anterior chamber and the second body region is a target outflow location within the patient's eye.

* * * * *